US007858089B2

(12) United States Patent
Jacquemin et al.

(10) Patent No.: US 7,858,089 B2
(45) Date of Patent: Dec. 28, 2010

(54) ANTIBODIES BINDING TO THE A2 DOMAIN OF FVIII AND INHIBITING COAGULATION ACTIVITY

(75) Inventors: Marc Jacquemin, Sart-Bernard (BE); Jean Guy Gilles, Brussels (BE); Jean-Marie Saint-Remy, Grez-Doiceau (BE)

(73) Assignee: Life Sciences Research Partners VZW, Leuven (BE)

( * ) Notice: Subject to any disclaimer, the term of this patent is extended or adjusted under 35 U.S.C. 154(b) by 44 days.

(21) Appl. No.: 11/997,283

(22) PCT Filed: Jul. 31, 2006

(86) PCT No.: PCT/EP2006/007564

§ 371 (c)(1),
(2), (4) Date: Jan. 29, 2008

(87) PCT Pub. No.: WO2007/017154

PCT Pub. Date: Feb. 15, 2007

(65) Prior Publication Data

US 2008/0206254 A1    Aug. 28, 2008

(30) Foreign Application Priority Data

Jul. 29, 2005  (GB)  ................... 0515637.7
Aug. 4, 2005  (GB)  ................... 0516055.1

(51) Int. Cl.
*A61K 39/00* (2006.01)
(52) U.S. Cl. .............. 424/133.1; 424/141.1; 424/145.1; 424/146.1; 514/13.7; 514/14.1
(58) Field of Classification Search ....................... None
See application file for complete search history.

(56) References Cited

U.S. PATENT DOCUMENTS 5,693,762 A * 12/1997 Queen et al. ............. 530/387.3
2004/0120951 A1   6/2004 Nakashima et al.

FOREIGN PATENT DOCUMENTS

| EP | 1 222 929 A2 | 7/2002 |
| EP | 1 396 539 A1 | 3/2004 |
| WO | WO 01/04269 A1 | 1/2001 |
| WO | WO 2005/046583 A2 | 5/2005 |

OTHER PUBLICATIONS van den Brink et al., Blood, 2000, 96:540-545.*
Rudikoff et al., Proc Natl Acad Sci U S A. Mar. 1982;79(6):1979-83.*
Janeway et al., Immunobiology, 3rd edition, 1997, Garland Press, pp. 3:1 to 3:11.*
William E. Paul, M.D. ed., Fundamental Immunology, 3d ed. 1993, p. 242.*
Portolano et al., J Immunol., 1993, 150:880-887.*
Aortic Regurgitation: Heart Valve Disorders: Merck Manual Home Edition, downloaded May 25, 2010.*
Marfan Syndrome:Hereditary Connective Tissue Disorders:: Merck Manual Home Edition, downloaded May 25, 2010.*
Communication from the European Patent Office issued in connection with European Patent Application No. 06 776 526.3, dated Feb. 4, 2010.
Davies et al., "Affinity improvement of single antibody VH domains: residues in all three hypervariable regions affect antigen binding," *Immunotechnology* 2: 169-179 (1996).
Healey et al., "Residues 484-508 Contain a Major Determinant of the Inhibitory Epitope in the A2 Domain of Human Factor VIII," *The Journal of Biological Chemistry* 270(24): 14505-14509 (1995).
Holt et al., "Domain antibodies: proteins for therapy," *TRENDS in Biotechnology* 21(11): 484-490 (2003).
Scandella et al., "Localization of Epitopes for Human Factor VIII Inhibitor Antibodies by Immunoblotting and Antibody Neutralization," *Blood* 74(5): 1618-1626 (1989).
Stoilova-McPhie et al., "3-Dimensional structure of membrane-bound coagulation factor VIII: modeling of the factor VIII heterodimer within a 3-dimensional density map derived by electron crystallography," *Blood* 99(4): 1215-1223 (2002).
Van den Brink et al., "Molecular analysis of human anti-factor VIII antibodies by V gene phage display identifies a new epitope in the acidic region following the A2 domain," *Blood* 96(2): 540-545 (2000).
International Search Report (PCT/EP2006/007564), mailed Jan. 30, 2007.
Written Opinion (PCT/EP2006/007564), mailed Jan. 30, 2007.
Response to the Written Opinion dated Jan. 30, 2007, mailed May 29, 2007.
Notification Concerning Informal Communication with the Applicant, mailed Sep. 10, 2007.
Response to "Notification Concerning Informal Communication with the Applicant," dated Sep. 17, 2007.
Notification of Transmittal of the International Preliminary Report on Patentability, mailed Oct. 11, 2007.

* cited by examiner

*Primary Examiner*—Michael Szperka
(74) *Attorney, Agent, or Firm*—Clark & Elbing LLP

(57) ABSTRACT

The present invention relates to new antibodies and fragments and derivatives thereof. These antibodies bind to the A2 domain of Factor VIII (FVIII) of the coagulation pathway and inhibit the coagulation activity of FVIII. The antibodies are particularly suited for the characterization of the structure and function of FVIII, for the design of therapeutic strategies for eradication of FVIII inhibitors and for the use as a medicament. The invention also relates to cell lines producing the specific antibodies. The present invention furthermore relates to pharmaceutical compositions comprising the antibodies, fragments and/or derivatives of the invention and to methods of preventing and treating cardiovascular disorders by using the antibodies or fragments and derivatives thereof or pharmaceutical compositions thereof.

11 Claims, 7 Drawing Sheets

Figure 1:
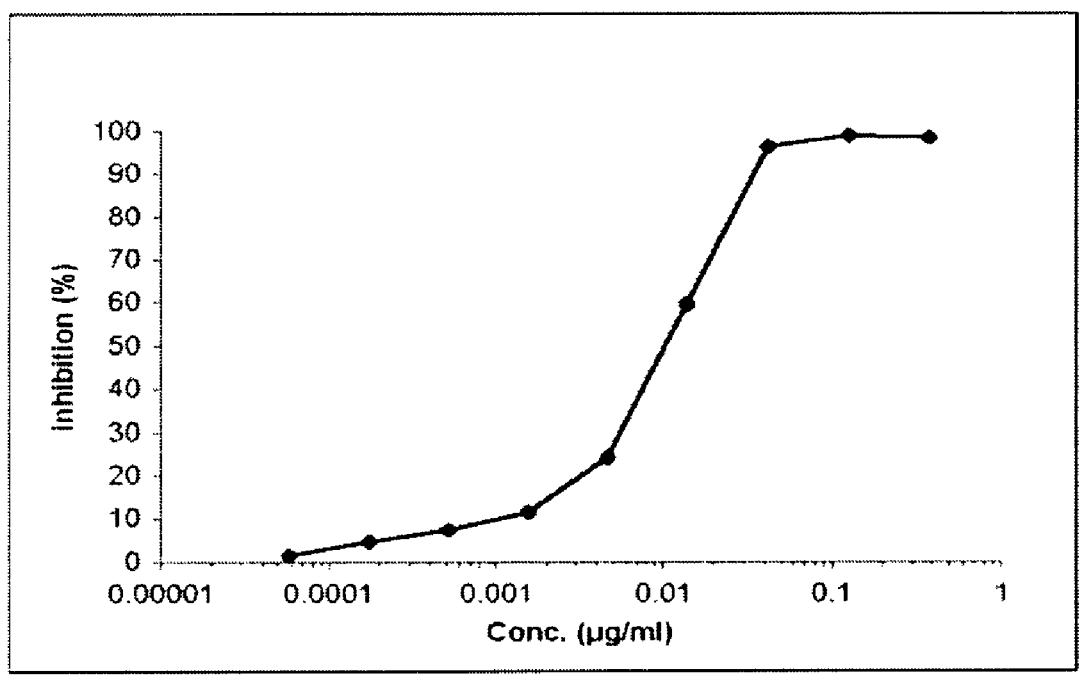

BOIIB2 heavy chain: SEQ ID NOS: 1 and 2
Font for alignment: Monaco 8

```
          ←------------------------Leader peptide-----------------------→
1         M   K   H   L   W   F   F   L   L   L   V   A   A   P   R   C   V   L   S   Q    20
1        ATG AAA CAC CTG TGG TTC TTC CTT CTC CTG GTG GCA GCT CCC AGA TGT GTC CTG TCC CAG   60

21        V   Q   L   Q   E   S   G   P   G   L   V   K   P   S   E   T   L   S   L   T    40
61       GTG CAG CTG CAG GAG TCG GGC CCA GGA CTG GTG AAG CCT TCG GAG ACC CTG TCC CTC ACC  120

←-------------CDR1--------------→
41        C   T   V   S   G   D   S   I   S   D   Y   Y   W   S   W   I   R   Q   P   P    60
121      TGC ACT GTC TCT GGT GAC TCC ATC AGT GAT TAC TAC TGG AGC TGG ATC CGG CAG CCC CCA  180

←---------------------CDR2------------------
61        G   K   G   L   E   W   I   G   Y   F   F   Y   S   G   G   S   N   Y   N   P    80
181      GGG AAG GGA CTG GAG TGG ATT GGC TAT TTT TTT TAC AGT GGG GGC AGC AAT TAC AAC CCC  240

-----------------→
81        S   L   K   S   R   V   T   M   S   V   D   T   S   K   N   Q   F   S   L   K   100
241      TCC CTC AAG AGT CGA GTC ACC ATG TCA GTA GAC ACA TCC AAG AAC CAG TTC TCC CTG AAG  300

←--------------
101       L   G   S   V   T   A   A   D   T   A   V   Y   Y   C   A   R   S   Q   L   R   120
301      CTG GGC TCT GTG ACC GCT GCG GAC ACG GCC GTC TAT TAC TGT GCG AGA TCG CAG TTA CGA  360

--CDR3-------------→                                     ------------------
121       Y   Y   L   D   V   W   G   Q   G   T   T   V   T   V   S   S   A   S   T   K   140
361      TAT TAC CTG GAC GTC TGG GGC CAA GGG ACC ACG GTC ACC GTC TCC TCG GCC TCC ACC AAG  420

------constante part start
141       G   P   S   V   F   P   L   A   P   C   S   R   S   T   S   E   S   T   A   A   160
421      GGC CCA TCG GTC TTC CCC CTG GCG CCC TGC TCC AGG AGC ACC TCC GAG AGC ACA GCG GCC  480

161       L   G   C   L   V   K   D   Y   F   P   E   P   V   T   V   S   W   N   S   G   180
481      CTG GGC TGC CTG GTC AAG GAC TAC TTC CCC GAA CCG GTG ACG GTG TCG TGG AAC TCA GGC  540

181       A   L   T   S   G   V   H   T   F   P   A   V   L   Q   S   S   G   L   Y   S   200
541      GCC CTG ACC AGC GGC GTG CAC ACC TTC CCG GCT GTC CTA CAG TCC TCA GGA CTC TAC TCC  600

201       L   S   S   V   V   T   V   P   S   S   S   L   G   T   K   T   Y   T   C   N   220
601      CTC AGC AGC GTG GTG ACC GTG CCC TCC AGC AGC TTG GGC ACG AAG ACC TAC ACC TGC AAT  660

221       V   D   H   K   P   S   N   T   K   V   D   K   R   V   E   S   K   Y   G   P   240
661      GTA GAT CAC AAG CCC AGC AAC ACC AAG GTG GAC AAG AGA GTT GAG TCC AAA TAT GGT CCC  720

241       P   C   P   S   C   P   A   P   E   F   L   G   G   P   S   V   F   L   F   P   260
721      CCA TGC CCA TCA TGC CCA GCA CCT GAG TTC CTG GGG GGA CCA TCA GTC TTC CTG TTC CCC  780

261       P   K   P   K   D   T   L   M   I   S   R   T   P   E   V   T   C   V   V   V   280
781      CCA AAA CCC AAG GAC ACT CTC ATG ATC TCC CGG ACC CCT GAG GTC ACG TGC GTG GTG GTG  840

281       D   V   S   Q   E   D   P   E   V   Q   F   N   W   Y   V   D   G   V   E   V   300
841      GAC GTG AGC CAG GAA GAC CCC GAG GTC CAG TTC AAC TGG TAC GTG GAT GGC GTG GAG GTG  900

301       H   N   A   K   T   K   P   R   E   E   Q   F   N   S   T   Y   R   V   V   S   320
901      CAT AAT GCC AAG ACA AAG CCG CGG GAG GAG CAG TTC AAC AGC ACG TAC CGT GTG GTC AGC  960
```

Figure 3

```
321  V   L   T   V   L   H   Q   D   W   L   N   G   K   E   Y   K   C   K   V   S   340
961  GTC CTC ACC GTC CTG CAC CAG GAC TGG CTG AAC GGC AAG GAG TAC AAG TGC AAG GTC TCC 1020

341  N   K   G   L   P   S   S   I   E   K   T   I   S   K   A   K   G   Q   P   R   360
1021 AAC AAA GGC CTC CCG TCC TCC ATC GAG AAA ACC ATC TCC AAA GCC AAA GGG CAG CCC CGA 1080

361  E   P   Q   V   Y   T   L   P   P   S   Q   E   E   M   T   K   N   Q   V   S   380
1081 GAG CCA CAG GTG TAC ACC CTG CCC CCA TCC CAG GAG GAG ATG ACC AAG AAC CAG GTC AGC 1140

381  L   T   C   L   V   K   G   F   Y   P   S   D   I   A   V   E   W   E   S   N   400
1141 CTG ACC TGC CTG GTC AAA GGC TTC TAC CCC AGC GAC ATC GCC GTG GAG TGG GAG AGC AAT 1200

401  G   Q   P   E   N   N   Y   K   T   T   P   P   V   L   D   S   D   G   S   F   420
1201 GGG CAG CCG GAG AAC AAC TAC AAG ACC ACG CCT CCC GTG CTG GAC TCC GAC GGC TCC TTC 1260

421  F   L   Y   S   R   L   T   V   D   K   S   R   W   Q   E   G   N   V   F   S   440
1261 TTC CTC TAC AGC AGG CTA ACC GTG GAC AAG AGC AGG TGG CAG GAG GGG AAT GTC TTC TCA 1320

441  C   S   V   M   H   E   A   L   H   N   H   Y   T   Q   K   S   L   S   L   S   460
1321 TGC TCC GTG ATG CAT GAG GCT CTG CAC AAC CAC TAC ACA CAG AAG AGC CTC TCC CTG TCT 1380

461  L   G   K   *   463
1381 CTG GGT AAA TGA 1392
``` heavy chain sequence details:

leader peptide: MKHLWFFLLLVAAPRCVLS    SEQ ID NO: 16
CDR1: GDSISDYYWS                     SEQ ID NO: 5
CDR2: YFFYSGGSNYNPSLKS               SEQ ID NO: 6
CDR3: SQLRYYLDV                      SEQ ID NO: 7
Start of CONSTANT PART: ASTK...      SEQ ID NO: 12

Figure 3 (continued)

BOIIB2 light chain: SEQ ID NOS: 3 and 4
Font for alignment: Monaco 8

```
      ←--------------------------Leader peptide-------------------------------→
1     M   E   T   P   A   Q   L   L   F   L   L   L   L   W   L   P   D   T   T   G    20
1     ATG GAA ACC CCA GCK CAG CTT CTC TTC CTC CTG CTA CTC TGG CTC CCA GAT ACC ACC GGA  60

21    E   I   V   L   T   Q   S   P   G   T   L   S   L   S   P   G   E   R   A   T    40
61    GAA ATT GTG TTG ACG CAG TCT CCA GGC ACC CTG TCT TTG TCT CCA GGG GAA AGA GCC ACC  120
                                    ←----------------CDR1-----------------→
41    L   S   C   R   A   S   Q   S   V   D   S   N   Y   L   A   W   Y   Q   Q   K    60
121   CTC TCC TGC AGG GCC AGT CAG AGT GTT GAC AGC AAC TAC TTA GCC TGG TAC CAG CAG AAA  180
                                            ←---------CDR2----------→
61    P   G   Q   A   P   R   V   V   I   Y   G   A   S   N   R   A   T   G   I   P    80
181   CCT GGC CAG GCT CCC AGG GTC GTC ATC TAT GGT GCA TCC AAC AGG GCC ACT GGC ATC CCA  240

81    D   R   F   S   G   S   G   S   G   T   E   F   T   L   T   I   S   R   L   D    100
241   GAC AGG TTC AGT GGC AGT GGG TCT GGG ACA GAG TTC ACT CTC ACC ATC AGC AGA CTG GAC  300
                                        ←---------CDR3---------→
101   P   E   D   F   A   V   Y   Y   C   Q   Q   Y   G   S   F   F   G   Q   G   T    120
301   CCT GAA GAT TTT GCA GTG TAT TAC TGT CAG CAG TAT GGT AGC TTC TTC GGC CAA GGG ACA  360
                        ------constant part start
121   R   L   E   I   K   R   T   V   A   A   P   S   V   F   I   F   P   P   S   D    140
361   CGA CTG GAG ATT AAA CGA ACT GTG GCT GCA CCA TCT GTC TTC ATC TTC CCG CCA TCT GAT  420

141   E   Q   L   K   S   G   T   A   S   V   V   C   L   L   N   N   F   Y   P   R    160
421   GAG CAG TTG AAA TCT GGA ACT GCC TCT GTT GTG TGC CTG CTG AAT AAC TTC TAT CCC AGA  480

161   E   A   K   V   Q   W   K   V   D   N   A   L   Q   S   G   N   S   Q   E   S    180
481   GAG GCC AAA GTA CAG TGG AAG GTG GAT AAC GCC CTC CAA TCG GGT AAC TCC CAG GAG AGT  540

181   V   T   E   Q   D   S   K   D   S   T   Y   S   L   S   S   T   L   T   L   S    200
541   GTC ACA GAG CAG GAC AGC AAG GAC AGC ACC TAC AGC CTC AGC AGC ACC CTG ACG CTG AGC  600

201   K   A   D   Y   E   K   H   K   V   Y   A   C   E   V   T   H   Q   G   L   S    220
601   AAA GCA GAC TAC GAG AAA CAC AAA GTC TAC GCC TGC GAA GTC ACC CAT CAG GGC CTG AGC  660

221   S   P   V   T   K   S   F   N   R   G   E   C   *   232
661   TCG CCC GTC ACA AAG AGC TTC AAC AGG GGA GAG TGT TAG 699
``` light chain sequence details:

leader peptide: METPAQLLFLLLLWLPDTTG    SEQ ID NO: 17
CDR1: SQSVDSNYLA                       SEQ ID NO: 8
CDR2: GASNRAT                          SEQ ID NO: 9
CDR3: QQYGSF                           SEQ ID NO: 10
Start of CONSTANT PART: RTVA...        SEQ ID NO: 13

Figure 3 (continued)

FVIII A2 domain with BOIIB2 epitope: SEQ ID NOS: 14 and 15
Font for alignement: Monaco 8

```
379  P   K   T   W   V   H   Y   I   A   A   E   E   E   D   W   D   Y   A   P   L   398
1135 cct aaa act tgg gta cat tac att gct gct gaa gag gag gac tgg gac tat gct ccc tta 1194

399  V   L   A   P   D   D   R   S   Y   K   S   Q   Y   L   N   N   G   P   Q   R   418
1195 gtc ctc gcc ccc gat gac aga agt tat aaa agt caa tat ttg aac aat ggc cct cag cgg 1254

419  I   G   R   K   Y   K   K   V   R   F   M   A   Y   T   D   E   T   F   K   T   438
1255 att ggt agg aag tac aaa aaa gtc cga ttt atg gca tac aca gat gaa acc ttt aag act 1314

439  R   E   A   I   Q   H   E   S   G   I   L   G   P   L   L   Y   G   E   V   G   458
1315 cgt gaa gct att cag cat gaa tca gga atc ttg gga cct tta ctt tat ggg gaa gtt gga 1374

459  D   T   L   L   I   I   F   K   N   Q   A   S   R   P   Y   N   I   Y   P   H   478
1375 gac aca ctg ttg att ata ttt aag aat caa gca agc aga cca tat aac atc tac cct cac 1434

479  G   I   T   D   V   R   P   L   Y   S   R   R   L   P   K   G   V   K   H   L   498
1435 gga atc act gat gtc cgt cct ttg tat tca agg aga tta cca aaa ggt gta aaa cat ttg 1494

499  K   D   F   P   I   L   P   G   E   I   F   K   Y   K   W   T   V   T   V   E   518
1495 aag gat ttt cca att ctg cca gga gaa ata ttc aaa tat aaa tgg aca gtg act gta gaa 1554

519  D   G   P   T   K   S   D   P   R   C   L   T   R   Y   Y   S   S   F   V   N   538
1555 gat ggg cca act aaa tca gat cct cgg tgc ctg acc cgc tat tac tct agt ttc gtt aat 1614

539  M   E   R   D   L   A   S   G   L   I   G   P   L   L   I   C   Y   K   E   S   558
1615 atg gag aga gat cta gct tca gga ctc att ggc cct ctc ctc atc tgc tac aaa gaa tct 1674

559  V   D   Q   R   G   N   Q   I   M   S   D   K   R   N   V   I   L   F   S   V   578
1675 gta gat caa aga gga aac cag ata atg tca gac aag agg aat gtc atc ctg ttt tct gta 1734

579  F   D   E   N   R   S   W   Y   L   T   E   N   I   Q   R   F   L   P   N   P   598
1735 ttt gat gag aac cga agc tgg tac ctc aca gag aat ata caa cgc ttt ctc ccc aat cca 1794

599  A   G   V   Q   L   E   D   P   E   F   Q   A   S   N   I   M   H   S   I   N   618
1795 gct gga gtg cag ctt gag gat cca gag ttc caa gcc tcc aac atc atg cac agc atc aat 1854

619  G   Y   V   F   D   S   L   Q   L   S   V   C   L   H   E   V   A   Y   W   Y   638
1855 ggc tat gtt ttt gat agt ttg cag ttg tca gtt tgt ttg cat gag gtg gca tac tgg tac 1914

639  I   L   S   I   G   A   Q   T   D   F   L   S   V   F   F   S   G   Y   T   F   658
1915 att cta agc att gga gca cag act gac ttc ctt tct gtc ttc ttc tct gga tat acc ttc 1974

659  K   H   K   M   V   Y   E   D   T   L   T   L   F   P   F   S   G   E   T   V   678
1975 aaa cac aaa atg gtc tat gaa gac aca ctc acc cta ttc cca ttc tca gga gaa act gtc 2034

679  F   M   S   M   E   N   P   G   L   W   I   L   G   C   H   N   S   D   F   R   698
2035 ttc atg tcg atg gaa aac cca ggt cta tgg att ctg ggg tgc cac aac tca gac ttt cgg 2094

699  N   R   G   M   T   A   L   L   K   V   S   S   C   D   K   N   T   G   D   Y   718
2095 aac aga ggc atg acc gcc tta ctg aag gtt tct agt tgt gac aag aac act ggt gat tat 2154

719  Y   E   D   S   Y   E   D   I   S   A   Y   L   L   S   K   N   N   A   I   E   738
2155 tac gag gac agt tat gaa gat att tca gca tac ttg ctg agt aaa aac aat gcc att gaa 2214

739  P   R   S   F   S   Q   N   S   R   H   P   S   T   R   Q   K   Q   F   N   A   758
2215 cca aga agc ttc tcc cag aat tca aga cac cct agc act agg caa aag caa ttt aat gcc 2274
``` details:

BOIIB2 epitope: 389 EEE 391 + 484 RPLYSRRLPKGVKHLKDFPILPGEI 508

SEQ ID NO:11

SEQUENCE LISTING

<160> NUMBER OF SEQ ID NOS: 17

<210> SEQ ID NO 1
<211> LENGTH: 351
<212> TYPE: DNA
<213> ORGANISM: Homo sapiens

<400> SEQUENCE: 1

```
caggtgcagc tgcaggagtc gggcccagga ctggtgaagc cttcggagac cctgtccctc      60
acctgcactg tctctggtga ctccatcagt gattactact ggagctggat ccggcagccc     120
ccagggaagg gactggagtg gattggctat ttttttaca gtgggggcag caattacaac     180
ccctccctca agagtcgagt caccatgtca gtagacacat ccaagaacca gttctccctg     240
aagctgggct ctgtgaccgc tgcggacacg gccgtctatt actgtgcgag atcgcagtta     300
cgatattacc tggacgtctg gggccaaggg accacggtca ccgtctcctc g              351
```

<210> SEQ ID NO 2
<211> LENGTH: 117
<212> TYPE: PRT
<213> ORGANISM: Homo sapiens

<400> SEQUENCE: 2

```
Gln Val Gln Leu Gln Glu Ser Gly Pro Gly Leu Val Lys Pro Ser Glu
1               5                   10                  15
Thr Leu Ser Leu Thr Cys Thr Val Ser Gly Asp Ser Ile Ser Asp Tyr
            20                  25                  30
Tyr Trp Ser Trp Ile Arg Gln Pro Pro Gly Lys Gly Leu Glu Trp Ile
        35                  40                  45
Gly Tyr Phe Phe Tyr Ser Gly Gly Ser Asn Tyr Asn Pro Ser Leu Lys
    50                  55                  60
Ser Arg Val Thr Met Ser Val Asp Thr Ser Lys Asn Gln Phe Ser Leu
65                  70                  75                  80
Lys Leu Gly Ser Val Thr Ala Ala Asp Thr Ala Val Tyr Tyr Cys Ala
                85                  90                  95
Arg Ser Gln Leu Arg Tyr Tyr Leu Asp Val Trp Gly Gln Gly Thr Thr
            100                 105                 110
Val Thr Val Ser Ser
        115
```

<210> SEQ ID NO 3
<211> LENGTH: 315
<212> TYPE: DNA
<213> ORGANISM: Homo sapiens

<400> SEQUENCE: 3

```
gaaattgtgt tgacgcagtc tccaggcacc ctgtctttgt ctccagggga aagagccacc      60
ctctcctgca gggccagtca gagtgttgac agcaactact tagcctggta ccagcagaaa     120
cctggccagg ctcccagggt cgtcatctat ggtgcatcca acagggccac tggcatccca     180
gacaggttca gtggcagtgg gtctgggaca gagttcactc tcaccatcag cagactggac     240
cctgaagatt ttgcagtgta ttactgtcag cagtatggta gcttcttcgg ccaagggaca     300
cgactggaga ttaaa                                                      315
```

<210> SEQ ID NO 4
<211> LENGTH: 105

```
<212> TYPE: PRT
<213> ORGANISM: Homo sapiens

<400> SEQUENCE: 4

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Asp Ser Asn
             20                  25                  30

Tyr Leu Ala Trp Tyr Gln Gln Lys Pro Gly Gln Ala Pro Arg Val Val
         35                  40                  45

Ile Tyr Gly Ala Ser Asn Arg Ala Thr Gly Ile Pro Asp Arg Phe Ser
     50                  55                  60

Gly Ser Gly Ser Gly Thr Glu Phe Thr Leu Thr Ile Ser Arg Leu Asp
 65                  70                  75                  80

Pro Glu Asp Phe Ala Val Tyr Tyr Cys Gln Gln Tyr Gly Ser Phe Phe
                 85                  90                  95

Gly Gln Gly Thr Arg Leu Glu Ile Lys
             100                 105

<210> SEQ ID NO 5
<211> LENGTH: 10
<212> TYPE: PRT
<213> ORGANISM: Homo sapiens

<400> SEQUENCE: 5

Gly Asp Ser Ile Ser Asp Tyr Tyr Trp Ser
 1               5                  10

<210> SEQ ID NO 6
<211> LENGTH: 16
<212> TYPE: PRT
<213> ORGANISM: Homo sapiens

<400> SEQUENCE: 6

Tyr Phe Phe Tyr Ser Gly Gly Ser Asn Tyr Asn Pro Ser Leu Lys Ser
 1               5                  10                  15

<210> SEQ ID NO 7
<211> LENGTH: 9
<212> TYPE: PRT
<213> ORGANISM: Homo sapiens

<400> SEQUENCE: 7

Ser Gln Leu Arg Tyr Tyr Leu Asp Val
 1               5

<210> SEQ ID NO 8
<211> LENGTH: 10
<212> TYPE: PRT
<213> ORGANISM: Homo sapiens

<400> SEQUENCE: 8

Ser Gln Ser Val Asp Ser Asn Tyr Leu Ala
 1               5                  10

<210> SEQ ID NO 9
<211> LENGTH: 7
<212> TYPE: PRT
<213> ORGANISM: Human

<400> SEQUENCE: 9

Gly Ala Ser Asn Arg Ala Thr
```

<210> SEQ ID NO 10
<211> LENGTH: 6
<212> TYPE: PRT
<213> ORGANISM: Homo sapiens

<400> SEQUENCE: 10

Gln Gln Tyr Gly Ser Phe
1               5

<210> SEQ ID NO 11
<211> LENGTH: 25
<212> TYPE: PRT
<213> ORGANISM: Homo sapiens

<400> SEQUENCE: 11

Arg Pro Leu Tyr Ser Arg Arg Leu Pro Lys Gly Val Lys His Leu Lys
1               5                   10                  15

Asp Phe Pro Ile Leu Pro Gly Glu Ile
            20                  25

<210> SEQ ID NO 12
<211> LENGTH: 4
<212> TYPE: PRT
<213> ORGANISM: Homo sapiens
<220> FEATURE:
<221> NAME/KEY: MISC_FEATURE
<222> LOCATION: (1)..(4)
<223> OTHER INFORMATION: start of constant part of the variable heavy
      chain of BOIIB2 antibody

<400> SEQUENCE: 12

Ala Ser Thr Lys
1

<210> SEQ ID NO 13
<211> LENGTH: 4
<212> TYPE: PRT
<213> ORGANISM: Homo sapiens
<220> FEATURE:
<221> NAME/KEY: MISC_FEATURE
<222> LOCATION: (1)..(4)
<223> OTHER INFORMATION: start of constant part of the variable light
      chain of BOIIB2 antibody

<400> SEQUENCE: 13

Arg Thr Val Ala
1

<210> SEQ ID NO 14
<211> LENGTH: 1140
<212> TYPE: DNA
<213> ORGANISM: Homo sapiens
<220> FEATURE:
<221> NAME/KEY: misc_feature
<222> LOCATION: (1)..(1140)
<223> OTHER INFORMATION: cDNA sequence of the A2 domain of Factor VIII

<400> SEQUENCE: 14
cctaaaactt gggtacatta cattgctgct gaagaggagg actgggacta tgctccctta    60
gtcctcgccc ccgatgacag aagttataaa agtcaatatt tgaacaatgg ccctcagcgg    120
attggtagga agtacaaaaa agtccgattt atggcataca cagatgaaac ctttaagact    180
cgtgaagcta ttcagcatga atcaggaatc ttgggacctt actttatggg ggaagttgga    240

-continued

```
gacacactgt tgattatatt taagaatcaa gcaagcagac catataacat ctaccctcac    300
ggaatcactg atgtccgtcc tttgtattca aggagattac caaaaggtgt aaaacatttg    360
aaggattttc caattctgcc aggagaaata ttcaaatata atggacagt gactgtagaa     420 gatgggccaa ctaaatcaga tcctcggtgc ctgacccgct attactctag tttcgttaat    480
atggagagag atctagcttc aggactcatt ggccctctcc tcatctgcta caaagaatct    540
gtagatcaaa gaggaaacca gataatgtca gacaagagga atgtcatcct gttttctgta    600
tttgatgaga accgaagctg gtacctcaca gagaatatac aacgctttct ccccaatcca    660
gctggagtgc agcttgagga tccagagttc caagcctcca acatcatgca cagcatcaat    720
ggctatgttt ttgatagttt gcagttgtca gtttgtttgc atgaggtggc atactggtac    780
attctaagca ttggagcaca gactgacttc ctttctgtct tcttctctgg atataccttc    840
aaacacaaaa tggtctatga agacacactc accctattcc cattctcagg agaaactgtc    900
ttcatgtcga tggaaaaccc aggtctatgg attctggggt gccacaactc agactttcgg    960
aacagaggca tgaccgcctt actgaaggtt tctagttgtg acaagaacac tggtgattat   1020
tacgaggaca gttatgaaga tatttcagca tacttgctga gtaaaaacaa tgccattgaa   1080
ccaagaagct tctcccagaa ttcaagacac cctagcacta ggcaaaagca atttaatgcc   1140
```

<210> SEQ ID NO 15
<211> LENGTH: 380
<212> TYPE: PRT
<213> ORGANISM: Homo sapiens
<220> FEATURE:
<221> NAME/KEY: MISC_FEATURE
<222> LOCATION: (1)..(380)
<223> OTHER INFORMATION: protein sequence of the A2 domain of human
      Factor VIII

<400> SEQUENCE: 15

```
Pro Lys Thr Trp Val His Tyr Ile Ala Ala Glu Glu Asp Trp Asp
1               5                   10                  15

Tyr Ala Pro Leu Val Leu Ala Pro Asp Asp Arg Ser Tyr Lys Ser Gln
            20                  25                  30

Tyr Leu Asn Asn Gly Pro Gln Arg Ile Gly Arg Lys Tyr Lys Lys Val
        35                  40                  45

Arg Phe Met Ala Tyr Thr Asp Glu Thr Phe Lys Thr Arg Glu Ala Ile
    50                  55                  60

Gln His Glu Ser Gly Ile Leu Gly Pro Leu Leu Tyr Gly Glu Val Gly
65                  70                  75                  80

Asp Thr Leu Leu Ile Ile Phe Lys Asn Gln Ala Ser Arg Pro Tyr Asn
                85                  90                  95

Ile Tyr Pro His Gly Ile Thr Asp Val Arg Pro Leu Tyr Ser Arg Arg
            100                 105                 110

Leu Pro Lys Gly Val Lys His Leu Lys Asp Phe Pro Ile Leu Pro Gly
        115                 120                 125

Glu Ile Phe Lys Tyr Lys Trp Thr Val Thr Val Glu Asp Gly Pro Thr
    130                 135                 140

Lys Ser Asp Pro Arg Cys Leu Thr Arg Tyr Tyr Ser Ser Phe Val Asn
145                 150                 155                 160

Met Glu Arg Asp Leu Ala Ser Gly Leu Ile Gly Pro Leu Leu Ile Cys
                165                 170                 175

Tyr Lys Glu Ser Val Asp Gln Arg Gly Asn Gln Ile Met Ser Asp Lys
            180                 185                 190
```

```
Arg Asn Val Ile Leu Phe Ser Val Phe Asp Glu Asn Arg Ser Trp Tyr
        195                 200                 205

Leu Thr Glu Asn Ile Gln Arg Phe Leu Pro Asn Pro Ala Gly Val Gln
    210                 215                 220

Leu Glu Asp Pro Glu Phe Gln Ala Ser Asn Ile Met His Ser Ile Asn
225                 230                 235                 240

Gly Tyr Val Phe Asp Ser Leu Gln Leu Ser Val Cys Leu His Glu Val
            245                 250                 255

Ala Tyr Trp Tyr Ile Leu Ser Ile Gly Ala Gln Thr Asp Phe Leu Ser
            260                 265                 270

Val Phe Phe Ser Gly Tyr Thr Phe Lys His Lys Met Val Tyr Glu Asp
        275                 280                 285

Thr Leu Thr Leu Phe Pro Phe Ser Gly Glu Thr Val Phe Met Ser Met
    290                 295                 300

Glu Asn Pro Gly Leu Trp Ile Leu Gly Cys His Asn Ser Asp Phe Arg
305                 310                 315                 320

Asn Arg Gly Met Thr Ala Leu Leu Lys Val Ser Ser Cys Asp Lys Asn
            325                 330                 335

Thr Gly Asp Tyr Tyr Glu Asp Ser Tyr Glu Asp Ile Ser Ala Tyr Leu
            340                 345                 350

Leu Ser Lys Asn Asn Ala Ile Glu Pro Arg Ser Phe Ser Gln Asn Ser
        355                 360                 365

Arg His Pro Ser Thr Arg Gln Lys Gln Phe Asn Ala
        370                 375                 380

<210> SEQ ID NO 16
<211> LENGTH: 19
<212> TYPE: PRT
<213> ORGANISM: Homo sapiens
<220> FEATURE:
<221> NAME/KEY: MISC_FEATURE
<222> LOCATION: (1)..(19)
<223> OTHER INFORMATION: leader peptide of BOIIB2 heavy chain

<400> SEQUENCE: 16

Met Lys His Leu Trp Phe Phe Leu Leu Leu Val Ala Ala Pro Arg Cys
1               5                   10                  15

Val Leu Ser

<210> SEQ ID NO 17
<211> LENGTH: 20
<212> TYPE: PRT
<213> ORGANISM: Homo sapiens
<220> FEATURE:
<221> NAME/KEY: MISC_FEATURE
<222> LOCATION: (1)..(20)
<223> OTHER INFORMATION: leader peptide of BOIIB2 light chain

<400> SEQUENCE: 17

Met Glu Thr Pro Ala Gln Leu Leu Phe Leu Leu Leu Leu Trp Leu Pro
1               5                   10                  15

Asp Arg Arg Gly
            20
```

ANTIBODIES BINDING TO THE A2 DOMAIN OF FVIII AND INHIBITING COAGULATION ACTIVITY

CROSS-REFERENCE TO RELATED APPLICATIONS

This application is the U.S. National Stage of International Application No. PCT/EP2006/007564, filed Jul. 31, 2006, which claims the benefit of British Patent Application No. 0515637.7 and British Patent Application No. 0516055.1, filed Jul. 29, 2005 and Aug. 4, 2005, respectively.

FIELD OF THE INVENTION

The present invention relates to new antibodies and fragments and derivatives thereof. The antibodies and fragments and derivatives thereof are particularly suited for the characterization of the structure and function of Factor VIII (FVIII) of the coagulation pathway, for the design of therapeutic strategies for eradication of FVIII inhibitors and for the use as a medicament. The invention also relates to cell lines producing the specific antibodies. The present invention furthermore relates to pharmaceutical compositions comprising the antibodies, fragments and/or derivatives of the invention and to methods of preventing and treating cardiovascular disorders by using the antibodies or fragments and derivatives thereof or pharmaceutical compositions thereof.

BACKGROUND OF THE INVENTION

The coagulation system in mammals is made of a series of proteins including pro-enzymes and co-factors interacting in a cascade type of activation. Upon activation, pro-enzymes convert into enzymes that, in the presence of the specific co-factor, cleave the next component in the cascade.

Such system is usually divided in three phases: an initiation phase, an amplification phase and a propagation phase. The initiation phase is triggered by the enzymatic cleavage of FX and FIX by tissue factor, in the presence of FVIIa and calcium. Activated FX cleaves prothrombin into thrombin. In the amplification phase thrombin activates a number of factors such as FV, FVIII and FXI, which in turn activates FIX. The propagation phase then is made of a number of positive feedback mechanisms, which result in further cleavage of FX by activated FIX combined with its co-factor FVIIIa. FXa and FVa associate to cleave prothrombin into thrombin.

Human FVIII is a 330 kd glycoprotein made of three domains containing two types of internal homologies. The first domain consists in the triplication of a A segment showing +/−30% homology between each other (A1, A2, A3) and encompassing residues 1-329, 380-711, 1,649-2,091, respectively. Regions A1 and A2 constitute the heavy chain, while A3, separated by a region of 948 amino acid rich in glycosylation sites (B domain) is located at the amino-terminal end of the light chain. The second internal homology is found at the carboxy-terminal end of the molecule where there are two copies of a third type of domain (C1 and C2) containing approximately 150 aminoacids with 40% homology. The native FVIII molecule made of the different segment separated by specific acidic regions (A1-a1-A2-a2-B-a3-A3-C1-C2) is rapidly cleaved by enzyme before entering in the plasma as an heterodimer consisting of a heavy chain (A1 and A2 domains together with the B domain or truncated part of it) associated by divalent cation to a 80 kD light chain (a3-A3-C1-C2). To become active and play its function in tenase complex formation, circulating FVIII has to be cleaved by thrombin.

Haemophilia A is characterized by the lack or insufficient function of FVIII. Patients with severe haemophilia A (namely, less than 1% functional FVIII), are treated by administration of recombinant or plasma-derived FVIII as a replacement therapy. About 25% of hemophilia A patients under replacement therapy by FVIII infusion develop an immune response to FVIII. This is due to the fact that severe haemophilia A patients have had no opportunity to become tolerant to FVIII because of lack of exposure of FVIII to their immune system during gestation. Anti-FVIII antibodies can also be found in the context of some autoimmune diseases, or occasionally after pregnancy or surgery. Such antibodies, called inhibitors, reduce the rate of thrombin generation by the tenase complex and thereby inhibit the amplification loop of the coagulation cascade.

Inhibitor antibodies recognize a number of discrete epitopes on the FVIII molecule. By far the most frequently recognized epitopes are located within the C2 and A2 domains. Extensive characterization of the epitopes in the C2 domain has been achieved thanks to the analysis of the crystal structure of C2 and to the availability of a human monoclonal anti-C2 antibody, which allowed a full validation of the structural model of the C2 domain, as well as a precise mapping of the epitope at single aminoacid level (Jacquemin M G et al., 1998 Blood. July 15; 92(2):496-506). This knowledge has opened two lines of investigations, namely the design of new FVIII molecules with reduced interaction with inhibitor antibodies and the development of new therapeutic strategies aiming at preventing or suppressing the production of anti-C2 inhibitor antibodies.

A similar approach to elucidate antibody interactions with the A2 domain has up to now been hampered by the lack of suitable reagent. The prior art described human monoclonal IgM antibodies with low affinities for the FVIII, but no human monoclonal IgG antibodies with strong FVIII inhibiting capacities have been described.

Antibodies derived from the repertoire of patients with inhibitors are unique reagents as they represent the actual antibodies generated towards FVIII. By contrast, antibodies raised in animal models such as the mouse are not representative of the human situation, as the characteristics of mouse immune system are not comparable to that of human.

Next to a potential use for characterization of FVIII or establishment of therapies aiming at preventing or suppressing the production of inhibitors, antibodies against the A2-domain of FVIII, whether or not derived from Hemophilia A patients, can also be useful for therapeutic purposes, e.g for inhibiting the formation of blood clots. Anticoagulation and antithrombotic treatment aim at inhibiting the formation of blood clots in order to prevent the dangerous consequences, such as myocardial infarction, stroke, loss of a limb by peripheral artery disease or pulmonary embolism. Until today, antithrombotic therapy relies on a few drugs since many years, namely Aspirin, heparin and oral Warfarin. With growing understanding of the processes involved in thrombosis a growing number of specific inhibitors of coagulation factors have been developed, such as recombinant tissue plasminogen activator (t-PA) or streptokinase. However, a better efficacy/safety ratio could to date not be obtained with them.

Monoclonal antibodies have already been shown to be of therapeutic value as antithrombotic agents. The first approved drug in this field was Abciximab (ReoPro™), a humanized Fab fragment of a murine monoclonal antibody (7E3) against platelet GP IIbIIIa receptors. Murine antibodies have characteristics which may severely limit their use in human therapy, since they may elicit an anti-immunoglobulin response termed human anti-mouse antibody (HAMA) that reduces or destroys their therapeutic efficacy and/or provokes allergic or hypersensitivity reactions in patients. While the use of human monoclonal antibodies would address this limitation, it has proven difficult to generate large amounts of such antibodies by conventional hybridoma technology.

Recombinant technology has therefore been used to construct "humanized" antibodies that maintain the high binding affinity of murine monoclonal antibodies but exhibit reduced immunogenicity in humans. Problems with binding affinity and side-effects like bleeding have been reported for several "humanized" antibody therapies.

Accordingly, novel anticoagulation and antithrombotic/thrombolytic treatments or in general compounds for the treatment of coagulation disorders are needed. For a therapeutic agent based on antibodies, the ideal compound is a human antibody with full anticoagulant efficacy that does not induce immunogenicity.

The prior art describes isolated human antibodies to the A2-domain of Factor VIII, obtained from lymphoblastoid cell lines producing anti-FVIII antibodies from peripheral blood mononuclear cells (PBMCs) of hemophilia A patients by EBV-immortalization (Gharagozlou et al. 2003, Human antibodies 12:67-76). All of the antibodies described are however exclusively of the IgM isotype and therefore difficult to use for therapeutic purposes. The authors furthermore suggest that there is a system of preferential expansion of the Factor-VIII-specific IgM+ B-cells in hemophiliac patients which could be specifically associated with the properties of FVIII molecules and the conditions of the sensitization to FVIII in hemophilia patients, hereby suggesting that obtaining IgG antibodies through this way is not possible or extremely difficult.

Accordingly, there remains a need for monoclonal antibodies and antibody fragments, which bind to the A2 domain of Factor VIII and inhibit FVIII activity. Ideally, for use as therapeutic agents, such antibodies are non-immunogenic, in that they can not elicit HAMA (or have a low tendency to do so).

SUMMARY OF THE INVENTION

The present invention provides the first human monoclonal IgG antibody directed to the A2 domain of FVIII, its production and full characterization, as well as its use for the structural and functional characterization of FVIII and for the use as a medicament. The present invention furthermore provides antibodies and antigen-binding fragments thereof which specifically bind the A2 domain of FVIII and are useful in research, diagnosis and therapy. We also provide a strategy for the design of a therapy aiming at suppressing the production of anti-A2 inhibitory antibodies.

A first aspect of the present invention relates to novel monoclonal antibodies, more specifically of the IgG isotype, and fragments and derivatives thereof directed to the A2 domain of Factor VIII. Particular embodiments of the monoclonal antibodies of the present invention inhibit the activity of Factor VIII.

A particular embodiment of this aspect of the invention more specifically provides human monoclonal antibodies of the IgG type, characterized in that the heavy chain of the variable region of the antibody comprises, in its CDRs, the sequences corresponding SEQ ID NO: 5 to 7 or sequences having at least 80% or at least 90% or 95% sequence identity and the light chain variable region comprises, in its CDRs the sequences of SEQ ID NO: 8 to 10 or sequences having at least 80% or at least 90% or 95% sequence identity therewith.

A further particular embodiment provides human monoclonal antibodies of the IgG type characterized in that their heavy chain variable region comprises the sequence of SEQ ID NO: 2 or a sequence having at least 80% or at least 90% or 95% sequence identity therewith within the CDR regions and/or their light chain variable region comprises the sequence of SEQ ID NO: 4 or a sequence having at least 80% or at least 90% or 95% sequence identity therewith within the CDR regions.

A further particular embodiment provides human monoclonal antibodies of the IgG type which are antobodies BOIIB2, produced by the cell line denosited with accession number LMBP 6422CB at the BCCM.

A further particular embodiment of this aspect of the invention provide antigen-binding fragments of the above-described human monoclonal IgG antibodies, which are selected from the group of Fab, Fab' or F(ab')$_2$, a diabody, a triabody a tetrabody, a minibody, a combination of at least two complementarity determining regions (CDRs), a soluble or membrane-anchored single-chain variable part, or single variable domain.

Another aspect of the invention provides the antibody BOIIB2 produced by the cell line deposited with accession number LMBP 6422CB at the BCCM, capable of specifically binding to the A2 domain of FVIII and any antibody which compete with antibody BOIIB2 for the binding to FVIII.

According to a specific embodiment, the antibodies antibody which compete with antibody BOIIB2 for the binding to FVIII specifically bind to the sequence of SEQ ID NO: 11.

According to a further specific embodiment the antibodies antibody which compete with antibody BOIIB2 for the binding to FVIII are human antibodies, camel antibodies, shark antibodies, or humanized antibodies, or chimeric antibodies. More particularly, the antibodies are monoclonal antibodies.

In particular embodiments of this aspect of the invention, the antibodies which compete with antibody BOIIB2 for the binding to FVIII are characterized in that the heavy chain of the variable region of the antibody comprises, in its CDRs, the sequences corresponding SEQ ID NO: 5 to 7 or sequences having at least 80% or at least 90% or 95% sequence identity and the light chain variable region comprises, in its CDRs the sequences of SEQ ID NO: 8 to 10 or sequences having at least 80% or at least 90% or 95% sequence identity therewith.

In further particular embodiments of this aspect of the invention, the antibodies which compete with antibody BOIIB2 for the binding to FVIII are characterized in that their heavy chain variable region comprises the sequence of SEQ ID NO: 2 or a sequence having at least 80% or at least 90% or 95% sequence identity therewith within the CDR regions and/or their light chain variable region comprises the sequence of SEQ ID NO: 4 or a sequence having at least 80% or at least 90% or 95% sequence identity therewith within the CDR regions In further particular embodiments the present invention provides antibody fragments, more particularly antigen-binding fragments of antibodies which compete with antibody BOIIB2 for the binding to FVIII, more particularly antibody fragments which compete with antibody BOIIB2 for the binding to FVIII. More specifically, these antibody fragments are selected from the group consisting of Fab, Fab' or F(ab')$_2$, a diabody, a triabody a tetrabody, a minibody, a combination of at least two complementarity determining regions (CDRs), a soluble or membrane-anchored single-chain variable part, or single variable domain.

Particular embodiments of such antigen-binding fragments include fragments which comprise at least two CDRs of BOIIB2 or derivatives thereof or more particularly at least two CDRs selected from the group of SEQ ID NO: 5 to 10 or which comprise at least two sequences having at least 80% or at least 90% or 95% sequence identity therewith. Specific embodiments of the antibody fragments of the present invention are fragments which comprise the sequence of SEQ ID NO: 6 and SEQ ID NO: 7 or a sequence having at least 80% or at least 90% or 95% sequence identity therewith or the sequence of SEQ ID NO: 9 and SEQ ID NO: 10 or a sequence having at least 80% or at least 90% or 95% sequence identity therewith.

A particular embodiment of the invention relates to the provision of single-chain variable fragments (scFvs) of the human BOIIB2 antibody and scFvs which are capable of inhibiting FVIII activity. Another embodiment of the present invention relates to antigen-binding derivatives of the antibodies of the invention, comprising conjugates of the antibodies with labels or peptides or other molecules of interest, polypeptides comprising one or more CDR's and others. According to a particular embodiment of the invention, the antibody is a hybrid antibody, most particularly a bivalent antibody which combines specificity for two different antigens or epitopes.

Yet a further object of the present invention is the provision of cell lines producing the antibodies of the present invention. This includes the cell lines producing the monoclonal human IgG antibodies and the cell lines producing the antibodies of the invention which compete with antibody BOIIB2 for the binding to FVIII. This also includes cell lines which are capable of producing the antibodies derived from BOIIB2 or fragments thereof, for instance as a result of recombinant technology. A particular embodiment of this aspect of the invention is the cell line named BOIIB2 producing monoclonal antibodies according to the present invention, which is deposited with the BCCM/LMBP with the accession number LMBP 6422CB (Belgian Co-ordinated Collections of Microorganisms/Plasmid Collection Laboratorium voor Moleculaire Biologie, University of Ghent K. L. Ledeganckstraat 35, B-9000 Ghent, B E).

Another aspect of the present invention relates to the use of the antibodies and antigen-binding fragments and derivatives of the present invention, namely for the immunological detection of FIII in human samples, i.e. as a diagnositic tool, as labelled targeting moieties in diagnostic methods, for the screening of compounds which inhibit FVIII activity, for the characterization of the structure and function of FVIII and for the design of therapeutic strategies for eradication of FVIII inhibitors inter alia in the identification of compounds that prevent and/or suppress the production or activity of anti-A2 inhibitor antibodies.

Another aspect of the present invention provides methods of treatment and/or prevention of cardiovascular disorders in a mammal, which methods comprise administering to a mammal, more in particular a human, in need of such treatment or prevention a therapeutically effective amount of an active ingredient which an antibody specifically binding to the A2 domain of FVIII according to the present invention or an antigen-binding fragment or derivative thereof. A particular embodiment of the method of the invention relates to the treatment and/or prevention of cardiovascular disorders such as, but not limited to disorders of hemostasis, in particular of the coagulation cascade and resulting thrombotic pathologic conditions in humans such as deep vein thrombosis, pulmonary embolism, stroke, myocardial infarction, disorders referred to as SIRS, including but not limited to systemic inflammation in pancreatitis, ischemia, multiple trauma and tissue injury, haemorrhagic shock, immune-mediated organ injury and infection, sepsis, septic shock, thrombus formation in the microvasculature, disseminated intravascular coagulation (DIC), septicemia and the like.

Another aspect of the invention relates to the use of the antibodies and fragments and derivatives thereof as a medicament and for the manufacture of a medicament for the prevention and/or treatment of coagulation disorders, such as, but not limited to cardiovascular disorders. In specific embodiments of the methods of the invention, the coagulation disorder is a thrombotic pathologic conditions in humans selected from the group consisting of deep vein thrombosis, pulmonary embolism, stroke, myocardial infarction and disorders referred to as SIRS (systemic inflammatory response syndrome).

The present invention also relates to the use of the antibodies and antigen-binding fragments and derivatives of the present invention to inhibit or reduce thrombin production by the intrinsic pathway as well as by the extrinsic pathway of coagulation.

Another aspect of the invention relates to pharmaceutical compositions of the antibodies of the invention or fragments or derivatives thereof and to methods of treatment of coagulation disorders by using the antibodies of the invention or fragments or derivatives thereof.

Particular embodiments of the pharmaceutical compositions for the prevention or treatment of coagulation disorders in mammals comprise an antibody against FVIII which is BOIIB2 or a fragment or derivative, more particularly an antigen-binding fragment thereof in admixture with a pharmaceutically acceptable carrier. A specific embodiment of the invention is a pharmaceutical composition which comprises an antigen-binding fragment of BOIIB2 or a derivative thereof, which is selected from the group consisting of an Fab, Fab' or $F(ab')_2$, a soluble or membrane-anchored single-chain variable part or a single variable domain. Most particular embodiments of the present invention relate to pharmaceutical compositions comprising an antigen-binding fragment which comprises at least two CDRs selected from the group of SEQ ID NO: 5 to 10 or at least two sequences having at least 80% or at least 90% or 95% sequence identity with two different sequences selected from the group of SEQ ID NO: 5 to 10. A particular embodiment thereof relates to pharmaceutical compositions comprising a scFv of the BOIIB2 antibody of the invention, more particularly comprising a scFv comprising at least two CDRs selected from the group of SEQ ID NO: 5 to 10 or at least two sequences having at least 80% or at least 90% or 95% sequence identity with two different sequences selected from the group of SEQ ID NO: 5 to 10.

In yet another particular embodiment of the pharmaceutical composition according to the invention, a therapeutically effective amount of another agent useful for the treatment or prevention of coagulation disorders is included in addition to the anti-FVIII antibody or antibody fragment of the invention. Most particularly in this respect, other anti-FVIII antibodies or fragments or derivatives thereof such as Krix-I are envisaged.

Another object of the invention relates to a process for the production of human monoclonal anti-FVIII antibodies of the IgG isotype, more in particular directed to the A2 domain of FVIII, more in particular binding to the epitope of BOIIB2, comprising the steps of first preparing memory IgG-bearing B cells from PBMC of hemophiliac patients, followed by activation of the memory B cells through the CD40 receptor and add EBV to immortalize the lines. Another embodiment relates to a process for the preparation of monoclonal anti-FVIII antibodies of the IgG isotype, more in particular directed to the A2 domain of FVIII, more in particular binding to the epitope of BOIIB2, via immunization of mammals, for example mice, with peptides comprising (at least) the sequence of SEQ. ID NO: 11. Such antibodies can than be humanized or fragments and derivatives can than be prepared from these mammalian antibodies.

Another aspect of the present invention provides polynucleotides encoding the antigen-binding fragments of the antibodies binding to FVIII disclosed herein, more particularly nucleotide sequences encoding the heavy and light chain variable regions of BOIIB2 produced by cell line BOIIB2. Most specifically the nucleotide sequence encoding the variable regions of SEQ ID NO: 2 and SEQ ID NO: 4 are envisaged. Additionally polynucleotide sequences encoding antigen-binding fragments comprising at least two CDRs of BOIIB2, more specifically, polynucleotides encoding at least two of the CDRs selected from the group consisting of SEQ ID NO: 5 to SEQ ID NO: 10 or encoding sequences comprising at least two CDRs having at least 80% or at least 90% or 95% sequence identity with SEQ ID NO: 5 to 10. Specific embodiments of the nucleotides of the present invention are provided in SEQ ID NOS 1 and 3. Further specific embodiments include the nucleotide sequences encoding the scFv of BOIIB2, and sequences having at least 80% or at least 90% sequence identity therewith, most particularly within the regions encoding the CDR regions of the scFv. It will be appreciated however that a multitude of nucleotide sequences exist which fall under the scope of the present invention as a result of the redundancy in the genetic code.

The invention further provides recombinant expression vectors encoding a peptide selected from the group consisting of SEQ ID NOs: 1, 3 and 5 to 10, more specifically bacterial, yeast, plant, mammalian or viral expression vectors; Additionally, the invention provides recombinant cells comprising the described vectors, more particularly human cells.

Another particular embodiment of the invention relates to the use of the epitope of BOIIB2 (epitope sequence SEQ ID NO: 11) of the present invention for the production of FVIII inhibiting antibodies directed to the A2 domain of Factor VIII or for the use in assays for the screening of compounds which inhibit FVIII.

DETAILED DESCRIPTION OF THE FIGURES

The following description including the examples, not intended to limit the invention to specific embodiments described, may be understood in conjunction with the accompanying Figures, incorporated herein by reference, in which:

FIG. 1: Evaluation of the capacity of the BOIIB2 to inhibit FVIII in a functional assay. Percentage of inhibition (Y axis) is calculated with regard to the positive control recFVIII 1 IU/ml. The curve indicates that BOIIB2 inhibits FVIII function up to 99% at a concentration of 0.1 µg/ml.

Figure 2:
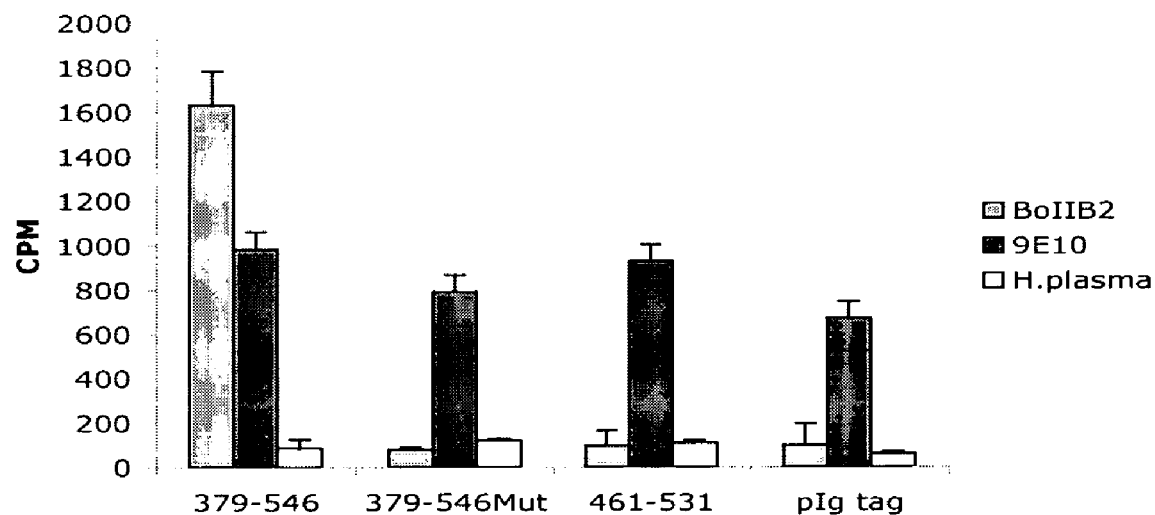

FIG. 2: BOIIB2 epitope mapping. Binding of antibody BoIIB2 ("BoIIB2"), anti-cmyc9E10 antibody ("9E10") and human plasma (obtained from healthy donors; "H. plasma") to A2 domain residues 379-546 ("379-546"), A2 domain residues 379-546 comprising a single mutation ("379-546Mut"), and A2 domain residues 461-531 ("461-531"), and a control Ig fragment ("pIg tag") each tagged with cmyc9E10. Results are means of duplicates and SD are indicated.

FIG. 3: Human Antibody (BOIIB2) sequence (nucleotide (SEQ ID NOS: 1 and 3) and amino acid (SEQ ID NOS: 2 and 4) sequence) with general identification of the sites of the variable and constant regions and the CDRs, including heavy chain leader peptide (SEQ ID NO: 16), CDR1 (SEQ ID NO: 5), CDR2 (SEQ ID NO: 6), CDR3 (SEQ ID NO: 7), and the start of the constant part (SEQ ID NO: 12); and light chain leader peptide (SEQ ID NO: 17), CDR1 (SEQ ID NO: 8), CDR2 (SEQ ID NO: 9), CDR3 (SEQ ID NO: 10), and the start of the constant part (SEQ ID NO: 13).

FIG. 4: Identification of the epitope of BOIIB2 (SEQ ID NO:11) in the A2 domain of Factor VIII (SEQ ID NOS: 14 and 15).

Figure 5:
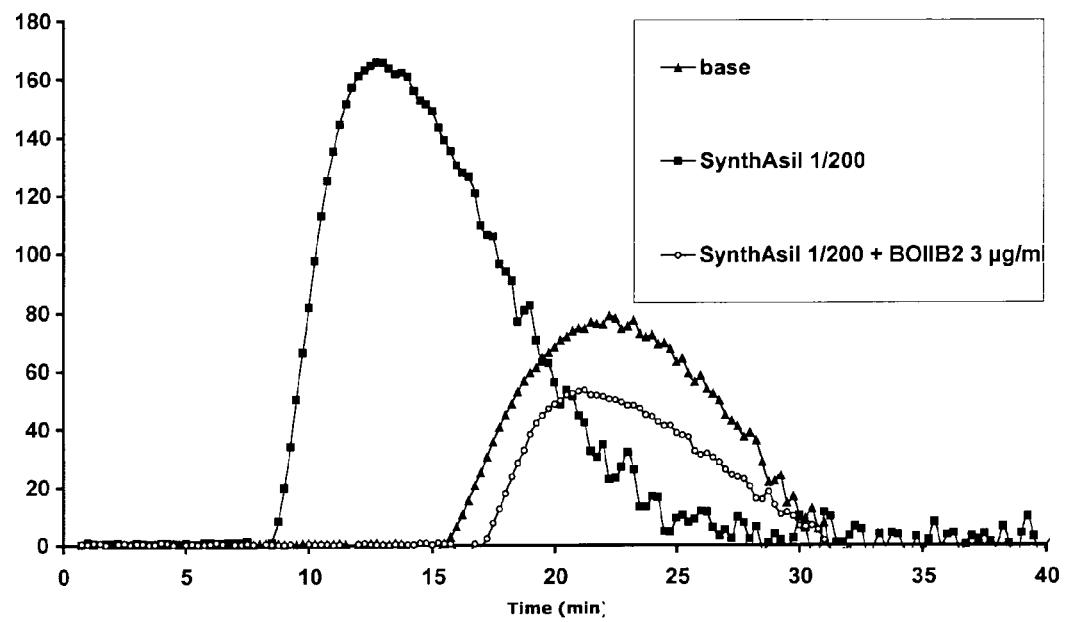

FIG. 5: Evaluation of the thrombin generation in a platelet rich plasma (PRP) upon activation of the intrinsic pathway of coagulation in the presence of the BOIIB2 antibody, as described in Example 6 herein. Thrombin activity in PRP based on detection of the release of fluorescent AMC from a thrombin substrate peptide was measured in the presence of SynthAsill/200 alone and SynthAsill/200+3 µg/ml of antibody BOIIB2.

Figure 6:
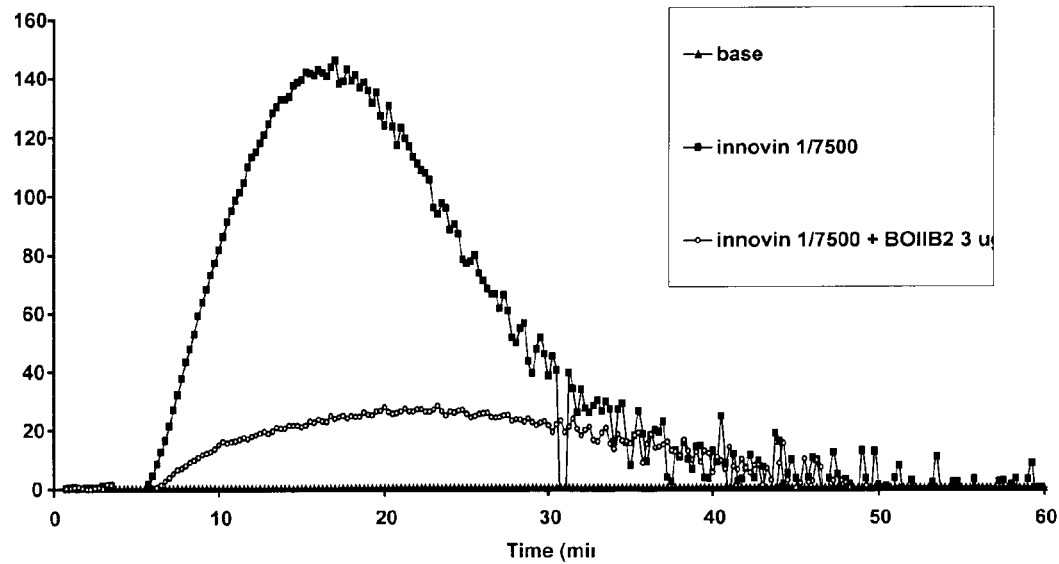

FIG. 6: Evaluation of the thrombin generation further to in a platelet rich plasma (PRP) upon activation of the extrinsic pathway of coagulation in the presence of the BOIIB2 antibody. Thrombin activity in PRP based on detection of the release of fluorescent AMC from a thrombin substrate peptide was measured in the presence of Innovin 1/7500 alone and Innovin 1/7500+3 µg/ml of antibody BOIIB2

DETAILED DESCRIPTION OF THE INVENTION

Definitions

The term "antibody fragment" as used herein refers to a sub-part of an antibody molecule or a molecule comprising one or more regions of an antibody which alone, or in combination with other fragments, is capable of binding to the antigen against which it was raised. Typical antibody fragments are Fab, Fab', F(ab')$_2$, single variable domains (Fv) or single chain variable part (or region) (scFv). Smaller fragments include complementarity determining regions or CDRs such as CDR1, CDR2 and CDR3 of the heavy or light chain and/or combinations of two or more thereof. Accordingly, the term "antibody fragment" encompasses both fragments which can be obtained by fragmentation of the intact antibodies and molecules obtained by recombinant technology comprising one or more parts (i.e. amino acid sequences) of the antibody, such as, but not limited to nanobodies, bis-scFv, diabodies, triabodies etc. (as described in Holliger and Hudson, Nature Biotechnology, 2005, 23(9):1126-1136).

The term "derivative" of an antibody or antibody fragment is used herein to refer to an antibody or antibody fragment which is the result of a modification of the original antibody (e.g. as produced by a hybridoma cell line) e.g. with respect to its amino acid sequence (e.g. for humanization, increasing the affinity to the antigen or binding to other molecules such as labels), but without significantly affecting the binding of the antibody or fragment to the antigen. Derivatives include alternative structures of one or more CDRs resulting in an antigen-binding molecule such as a synthetic polypeptide. Derivatives include humanized versions of non-human antibodies, hybrid antibodies and antibodies or other antigen-binding molecules which have been obtained by grafting or introducing one or more of the variable regions and/or CDRs of one or more antibodies. Thus a derivative of a human antibody includes antibodies from a non-human species, comprising one or more of the variable regions and/or CDRs of that antibody, such as but not limited to hybrid camelid or nurse shark antibodies or nanobodies obtained therefrom. Additionally the term 'derivatives' includes antibodies and antibody fragments which have been modified with respect to glycosylation.

A "humanized antibody or humanized antibody fragment" as used herein, refers to a non-human antibody molecule or fragment thereof in which amino acids have been replaced in order to more closely resemble a human antibody. Typically, the majority of these substitutions will be in regions not contributing in antigen binding. Often the substitutions will be in the framework regions, between the CDRs. However, it is envisaged that within the CDRs, amino acids which do not or hardly take part in the binding to the antigen can also be substituted to more closely resemble a human antibody.

A "Reshaped" antibody or antibody fragment or a "hybrid antibody" as used herein, refers to an antibody which comprises parts of at least two different antibodies, more particularly two antibodies of a different species. Typically, a human hybrid antibody can be a human constant region linked to a non-human (optionally humanized) variable region of another antibody directed against the antigen of interest. or a human antibody backbone in which amino acid sequences in the antigen binding regions have been replaced with sequences from another antibody e.g. directed against a human antigen of interest. More particularly the antigen-binding regions of an antibody having an affinity for an antigen of interest, such as one or more CDRs or variable regions or parts thereof are introduced into the backbone of a human antibody (e.g. CDR-grafted antibodies). Where CDRs of antibodies directed against different epitopes are introduced (e.g. in each of the arms of the antibody, reshaped or hybrid antibodies can have affinities for two different epitopes of one antigen or even have affinity against different epitopes corresponding to different antigens.

The term "homology" or "homologous" as used herein with reference to antigen-binding molecules of the present invention refers to a molecule which will compete with or inhibit binding of that antigen-binding molecule to its antigen. The binding should be specific, i.e. the binding of the homologous molecule to the antigen should be as specific as the binding of the antigen-binding molecule to the antigen.

The term "sequence identity" of two nucleotide or amino acid sequences as used herein relates to the number of positions with identical nucleotides or amino acids divided by the number of nucleotides or amino acids in the shorter of the sequences, when the two sequences are aligned. Sequence identity between two sequences can be between 70%-80%, between 81-85%, between 86-90%, between 91-95%, or between 96-100%. In view of the generally limited contribution of the backbone of the variable regions to the binding with the antigen, sequence identity will most commonly be specified herein with regard to the amino acid sequence within the complementarity determining regions or CDRs, or with regard to the nucleotide sequences encoding and the amino acid sequences which constitute the CDRs.

Two amino acids are considered as "similar" if they both belong to one and the same of the following groups GASTCP; VILM; YWF; DEQN; KHR. Thus, the percentage of sequence similarity between two protein sequences as referred to herein can be determined by aligning the two protein sequences and determining the number of positions with identical or similar amino acids divided by the total number of amino acids in the shorter of the sequences.

The term "inhibitory" when referring to an antibody to FVIII or fragment or derivative thereof is used to indicate that the antibody, fragment or derivative is capable of inhibiting the function of FVIII, more particularly the function of FVIII in the coagulation cascade. The function of factor VIII is as following: FVIII acts as a cofactor of coagulation. Upon production of an initial burst of thrombin, FVIII is cleaved in its active form (FVIIIa) and dissociates from its chaperone molecule, von Willebrand factor. FVIIIa is then fully available for participating in the formation of a complex with activated factor IX (FIXa), which cleaves factor X to form FXa. The complex is called "tenase complex" based on its activity. The binding of FVIIIa to FIXa increases by ±100,000-fold the enzymatic activity of FIX. The formation of FXa, in combination with activated factor V, leads to the transformation of prothrombin into thrombin and subsequent formation of fibrin leading to coagulation. Accordingly, inhibition of FVIII activity generally results in reduced formation of thrombin, fibrin, and reduced coagulation, which can be measured by the methods described herein. Inhibition of FVIII can be a result of one or more of the following effects: inhibition of activation into FVIIIa, inhibition of the dissociation of VIII from vWF, inhibition of complex formation with FIXa.

The terms "Coagulation disorders" as used herein refers to disorders of hemostasis, in particular of the coagulation cascade and resulting thrombotic pathologic conditions in humans such as deep vein thrombosis, pulmonary embolism, stroke, myocardial infarction, disorders referred to as SIRS (systemic inflammatory response syndrome). Systemic inflammation is the possible endpoint of a number of clinical conditions including pancreatitis, ischemia, multiple trauma and tissue injury, haemorrhagic shock, immune-mediated organ injury and infection. Since quite comparable pathological changes are observed in systemic inflammation independently of the initial cause, the term "systemic inflammatory response syndrome" (hereinafter referred as SIRS) has been commonly quoted to account for such changes and is therefore used in the present application in accordance with the recommendations of the American College of Chest Physicians as formulated by R. C. Bone et al. in *Chest*(1992) 101:1644-55. The term "systemic inflammatory response syndrome (SIRS)" includes sepsis, septic shock, thrombus formation in the microvasculature, disseminated intravascular coagulation (DIC), septicemia and the like.

Nucleic acids referred to herein as "recombinant" are nucleic acids which have been produced by recombinant DNA methodology, including those nucleic acids that are generated by procedures which rely upon a method of artificial recombination, such as the polymerase chain reaction (PCR) and/or cloning into a vector using restriction enzymes. "Recombinant" nucleic acids are also those that result from recombination events that occur through the natural mechanisms of cells, but are selected for after the introduction to the cells of nucleic acids designed to allow and make probable a desired recombination event.

Detailed Description

The present invention will be described with reference to certain embodiments and to certain figures but the present invention is not limited thereto but only by the claims. The present invention is based on the surprising determination of new ligands, namely new monoclonal antibodies and fragments, derivatives and homologs thereof, more in particular of the IgG isotype, which inhibit FVIII through binding to the A2-domain.

The present invention relates to antibodies and antigen binding fragments thereof directed to factor VIII (FVIII). Human Factor VIII is a 330 kd glycoprotein made of three domains containing two types of internal homologies. The first domain consists in the triplication of a A segment showing +/−30% homology between each other (A1, A2, A3) and encompassing residues 1-329, 380-711, 1,649-2,091, respectively. Regions A1 and A2 constitute the heavy chain, while A3, separated by a region of 948 amino acid rich in glycosylation sites (B domain) is located at the amino-terminal end of the light chain. The second internal homology is found at the carboxy-terminal end of the molecule where there are two copies of a third type of domain (C1 and C2) containing approximately 150 amino acids with 40% homology. The native FVIII molecule made of the different segment separated by specific acidic regions (A1-a1-A2-a2-B-a3-A3-C1-C2) is rapidly cleaved by enzyme before entering in the plasma as an heterodimer consisting of a heavy chain (A1 and A2 domains together with the B domain or truncated part of it) associated by divalent cation to a 80 kD light chain (a3-A3-C1-C2). To became active and play its function in tenase complex formation, circulating FVIII has to be cleaved by thrombin.

The present invention describes and provides the production, characterization and use of purified/isolated antibodies specific for the A2 domain of FVIII and which inhibit the FVIII function.

Such inhibitory antibodies against Factor VIII and particularly against the A2 domain of Factor VIII, fragments and derivatives thereof can be used for different purposes. They can be used for the characterization of the structure and function of FVIII, for the design of therapeutic strategies for eradication of FVIII inhibitors, for the immunological detection of FIII in human samples, as targeting moieties in diagnostic methods (i.e. labeled antibodies), for the screening of compounds which inhibit FVIII or in general as a research reagent. In this way they are unique reagents as they represent the actual antibodies generated towards FVIII.

As an example of design of therapeutic strategies for eradication of FVIII inhibitors, peptides which have the capacity to bind to anti-A2 inhibitor antibodies and neutralize their inhibitory properties could be produced. Peptides for such purposes can be obtained by screening with phage-displayed random peptides such as described in Villard S et al. Blood (2003) 102: 949-952. The screening for compounds (i.e. small molecules, peptides, etc.) which can neutralize antibodies which inhibit the function of Factor VIII through interaction with the A2 domain can be performed using the antibodies of the invention. Additionally or alternatively peptides capable of inhibiting anti-Factor VIII antibodies can be generated using the epitope of BOIIB2 as template. This would include steps as known by a person skilled in the art, namely producing peptides with a sequence homologuous to the epitope sequence and followed by testing the inhibitory capacity.

The antibodies of the invention can furthermore be used for the purification of Factor VIII from human samples by using the antibody in a column for purification of human samples.

The antibodies of the present invention can furthermore also be used as a medicament and for the manufacture of a medicament for the prevention and/or treatment of coagulation disorders. For this use as a medicament, doses of the antibody should optimally be established which do not elicit bleeding of the mammals ensuring that Factor VIII is not 100% inhibited.

A first aspect of the present invention relates to antibodies to FVIII, more particularly human IgG antibodies directed to the A2 domain of factor VIII and antigen-binding fragments thereof.

As an example, the human antibody BOIIB2 is described, which is a monoclonal IgG antibody which has been obtained from the repertoire of natural memory B cells of a haemophilia A patient with inhibitor. Antibody BOIIB2 binds specifically to the A2 domain of FVIII, more particularly to an epitope corresponding to amino acids 379-546 therein and inhibits FVIII activity, more particularly inhibits FVIII procoagulant activity, as measured by the generation of thrombin in platelet rich plasma (PRP) upon activation of the extrinsic or intrinsic coagulation pathway.

Thus, a particular embodiment of this aspect of the invention provides antibodies which are intact IgG antibodies, more in particular IgG4 antibodies, directed to the A2 domain of factor VIII. It has been found that, by Methods for obtaining human IgG antibodies are described herein and constitute a further aspect of the invention.

Accordingly a second aspect of the present invention provides antibodies to FVIII, directed to the A2 domain of factor VIII and antigen-binding fragments thereof capable of competing with antibody BOIIB2 in the binding to FVIII. Particular embodiments of this aspect of the invention relate to antibodies and antigen binding fragments capable of competing with antibody BOIIB2 in the binding to FVIII and which inhibit FVIII activity.

Antibodies capable of competing with antibody BOIIB2 can be identified in different ways, by methods known to the skilled person. For example, the ability of an antibody to compete with BOIIB2 for the binding to FVIII can be tested in an ELISA, whereby FVIII binding to the antibody is tested with or without pre-incubation of FVIII with BOIIB2 or the antibody, as described in the Examples section herein. Accordingly, antibodies, obtained either by classical immunization methods and monoclonal antibody techniques or antibodies obtained from Hemophilia A patients with inhibitor, which bind to FVIII can be tested to determine competition with antibody BOIIB2.

According to a particular embodiment, the present invention provides antibodies, particularly monoclonal antibodies, or fragments or derivatives thereof, including humanized antibodies and antibody fragments which bind to the same epitope of FVIII as the antibody referred to herein as BOIIB2. More in particular, the epitope to which the antibodies bind is a conformational epitope, most particularly an epitope which comprises the amino acid residues between positions 484 and 508 and the glutamic acid residues 389, 390 and 391 of Factor VIII. In a particular embodiment the antibodies and fragments of the present invention bind to a protein or peptide comprising SEQ ID NO: 11.

Specific embodiments of the invention include human monoclonal antibody BOIIB2, produced by the cell line deposited under accession number LMBP 6422CB at the BCCM, and fragments or derivatives thereof including fragments and derivatives which may be produced, for example, by recombinant technology. The antibody BOIIB2 is directed against FVIII of human origin, binds human FVIII and inhibits the function of human FVIII and can thus be used for the inhibition of FVIII both in a therapeutic context and for testing or screening purposes.

Further embodiments of the present invention relate to monoclonal antibodies having substantially the same characteristics as antibody BOIIB2, more specifically being produced by on purpose immunization in animals, preferably in mouse, for instance by injecting FVIII in mice and then fusing the spleen lymphocytes with a mouse myeloma cell line, followed by identifying and cloning the cell cultures producing anti-FVIII antibodies. Optionally further selection of the antibodies is performed based on reactivity with the BOIIB2 epitope. Alternatively, animals could be immunized with the BOIIB2 epitope, for example by injecting the peptide with the sequence of the epitope and such antibodies can than further be humanized.

Another embodiment of the present invention relates to monoclonal antibodies having substantially the same characteristics as antibody BOIIB2 and being obtained from haemophiliac patients by using the method as described herein, namely by performing the following steps:

first preparing memory IgG-bearing B cells from PBMC of hemophiliac patients;

followed by activation of the memory B cells through the CD40 receptor by using an, immobilized CD40 ligand, as for instance on transfected cell lines, to cross-react with CD40;

add EBV to immortalize the cell lines.

A further aspect of the invention relates to antibodies and antigen-binding fragments thereof derived from monoclonal antibody BOIIB2 produced by the cell line deposited under accession number LMBP 6422CB at the BCCM capable of binding FVIII and inhibiting FVIII activity. Antibodies derived from antibody BOIIB2 typically comprise at least two CDRs of BOIIB2. Typically antigen-binding is determined primarily by CDR2 and CDR3 of the heavy and light chain variable regions. In further particular embodiments, derivatives of antibody BOIIB2 comprise a heavy and/or variable light chain region of antibody BOIIB2. The amino acid sequence of the variable regions of the heavy and light chains of antibody BOIIB2 are disclosed in SEQ ID NO: 2 and SEQ ID NO: 4, respectively.

Further embodiments of the invention relate to antibodies derived from antibody BOIIB2, comprising a variable heavy chain region and or a variable light chain region having at least 80%, particularly at least 85%, more particularly at least 90%, most particularly at least 95% sequence identity with SEQ ID NO:2 and/or SEQ ID NO:4 respectively.

Different types of derivatives of antibody BOIIB2 are envisaged within the context of the present invention. Accordingly, the present invention also relates to hybrid antibodies or chimeric antibodies or bivalent antibodies (i.e. wherein two different specificities are combined). Particular embodiments of the invention relate to hybrid antibodies comprising variable heavy and/or light chain regions of FIG. 3 or parts thereof and antibodies comprising at least two, more particularly three to five, most particularly all six CDRs of SEQ ID NO: 5 to SEQ ID NO: 10. Alternatively, the present invention provides hybrid antibodies comprising at least two, more particularly three to five, most particularly six CDRs having at least 80%, particularly at least 85%, more particularly at least 90%, most particularly at least 95% sequence identity with SEQ ID NO:5 to 10, respectively.

Methods for associating the binding complementarity determining region ("CDR") from different antibodies are known to the skilled person [see for instance, Recombinant approaches to IgG-like bispecific antibodies, Marvin J S and Zhu Z in Acta Pharmacologica Sinica, 2005, 26: 649-658]. Alternatively replacement of a more limited number of amino acids of the non-human anti-FVIII antibodies of the invention is also envisaged.

Yet another aspect provides functional fragments of antibodies of the present invention, including fragments of derivatives of the antibodies of the invention, including fragments of chimeric or humanized antibodies. Functional fragments of the antibodies described herein retain at least one binding function and/or modulation function of the full-length antibody from which they are derived. Particular functional fragments retain an antigen binding function of a corresponding full-length antibody (e.g., specificity for the A2 domain of FVIII). Particular functional fragments retain the ability to inhibit one or more functions characteristic of FVIII., such as its pro-coagulant activity. According to a specific embodiment, the present invention relates to antibody fragments such as Fab, Fab', F(ab')$_2$, combinations of two or more CDRs, peptides comprising two or more of the antibody CDRs, or single variable domains of the FVIII-binding antibodies of the present invention, such as BOIIB2. Such fragments can be produced by enzymatic cleavage or by recombinant techniques. Fab, Fab' and F(ab')$_2$ fragments can be generated by proteolytic digestion of monoclonal antibodies using methods well known in the art, such as described by Stanworth et al., *Handbook of Experimental Immunology* (1978), vol. 1 chapter 8 (Blackwell Scientific Publications). Such fragments, which retain the ability to bind the antigen, have lost a number of properties of the parent antibody, such as complement activation or capacity to bind to Fc gamma receptors. More specifically the present invention provides the variable regions of the heavy and light chains of BOIIB2 corresponding to SEQ ID NO: 2 and SEQ ID NO: 4 respectively, and derivatives thereof. A further particular embodiment of the invention relates to the complementarity determining regions (CDRs) of BOIIB2 and derivatives thereof. The two most commonly followed methods for identifying CDRs are IMGT and KABAT, and fragments comprising more than one of either type of CDR of BOIIB2 are envisaged within the context of the invention, as well as derivatives of BOIIB2 comprising these fragments or CDRs. According to the IMGT identification of CDRs, the CDR regions within the variable regions of BOIIB2 correspond to SEQ ID Nos: 5-10.

A further embodiment of the present invention relates to antibody fragments comprising a heavy chain variable region and/or a light chain region having at least 80%, particularly at least 85%, more particularly at least 90%, most particularly at least 95% sequence identity with SEQ ID NO: 2 and SEQ ID NO: 4, respectively within the CDR regions. Sequence identity within the framework regions can be, but is not limited to, less than 80%. Also envisaged are antibody fragments comprising at least two CDRs which have at least 80%, particularly at least 85%, more particularly at least 90%, most particularly at least 95% sequence identity with the sequences of SEQ ID NO: 5 to 10, respectively.

A further specific embodiment of the invention provides soluble or membrane anchored single-chain variable parts of the monoclonal antibodies to FVIII, more specifically BOIIB2. A single-chain variable fragment (scFv) is a genetically engineered antibody fragment that ususally consists of the variable heavy chain (VH) and light chain (VL) of an immunoglobulin, or parts thereof, joined together by a flexible peptide linker. Optionally, scFvs comprise the CDR regions of the antibody of interest and framework regions of another antibody. Methods for obtaining single-chain variable parts of antibodies are known to the skilled person. For instance the method can include amplification of the DNA sequences of the variable parts of human heavy and light chains in separated reactions and cloning, followed by insertion of a fifteen amino-acid linker sequence, for instance (Gly4 Ser)3 between VH and VL by a two-steps polymerase chain reaction (PCR) (see for instance Dieffenbach and Dveksler, "PCR Primer, a laboratory manual" (1995), Cold Spring Harbour Press, Plainview, N.Y., USA). The resulting fragment can then be inserted into a suitable vector for expression of single-chain fragment variable fragment (scFv) as soluble or phage-displayed polypeptide. This can be achieved by methods well known to those skilled in the art, such as described by Gilliland et al., *Tissue Antigens* (1996) 47:1-20.

The present invention also provides peptides representative of the hypervariable regions of a monoclonal antibody or combinations thereof, capable of binding FVIII. Such peptides can be obtained by synthesis using an applied biosystem synthesizer, for instance a polypeptide synthesizer such as model 9050 available from Milligen (USA) or a model from a related technology.

A further aspect of the present invention also relates to a process for the preparation of human monoclonal anti-FVIII antibodies of the IgG isotype, more in particular directed to the A2 domain of FVIII, including antibodies binding to the epitope of BOIIB2 and inhibiting the function of FVIII, which methods comprise the steps of first preparing memory B cells from PBMC of hemophiliac patients which bear IgG antibodies, followed by activation of the memory B cells through the CD40 receptor and add EBV to immortalize the lines.

The method used for the production of human monoclonal anti-FVIII antibodies of the IgG isotype differs from the one described by Gharagozlou et al (Hum Antibodies. 2003; 12(3):67-76) as follows:
(1) the first step consists in sorting IgG-bearing B cells from PBMC obtained from patients with inhibitor to FVIII. Thus, IgM-bearing B cells are depleted by adsorption on magnetic beads carrying an anti-human IgM antibody. Antibodies prepared by Gharagozlou et al are made directly from PBMC and specifically target IgM-bearing B cells, which are the only peripheral blood B cells susceptible to be transformed with EBV;

(2) IgG-bearing B cells (memory B cells) are then exposed to a cell line, usually a fibroblast cell line, which has been transfected with the ligand for human CD40 (CD40L). This allows to overcome the initial apoptosis of B cells during culture, as activation of CD40 at the surface of B cells transduces a survival signal. This step is missing in Gharagozlou et al's description.

Another embodiment of the methods of the present invention relates to a process for the preparation of monoclonal anti-FVIII antibodies of the IgG isotype, more in particular directed to the A2 domain of FVIII, such as antibodies binding to the epitope of BOIIB2, via immunization of mammals, for example mice, with peptides comprising the whole epitope sequence or the sequence of SEQ. ID NO: 11. Peptides used for this purpose can furthermore comprise other amino acids.

Yet another aspect of the present invention thus relates to cell lines producing the anti-human FVIII antibodies of the invention, more particularly cell lines producing monoclonal antibody BOIIB2 or fragments or derivatives thereof. A particular embodiment of this aspect of the invention is the hybridoma cell line named BOIIB2 producing human monoclonal antibodies of the IgG isotype according to the present invention. The cell line BOIIB2 has been deposited with the BCCM/LMBP with the accession number LMBP 6422CB (Belgian Co-ordinated Collections of Microorganisms/Plasmid Collection Laboratorium voor Moleculaire Biologie, University of Ghent K. L. Ledeganckstraat 35, B-9000 Ghent, B E) on Aug. 4, 2005 by the inventor Marc Jacquemin. The present invention further provides cell lines producing human monoclonal antibodies capable of competing for the binding with FVIII with human monoclonal antibody BOIIB2 obtained from the above-mentioned cell line BOIIB2 as described herein.

Yet another aspect of the present invention relates to the provision of nucleotides encoding the variable heavy or variable light chain regions of antibody BOIIB2 or the fragments or derivatives thereof, such as those obtainable from the cell line BOIIB2. Particular embodiments of the invention relate to the nucleotide sequences encoding the variable heavy chain region and the light chain variable region defined by SEQ ID NO: 2 and SEQ ID NO:4, respectively, such as, but not limited to the nucleotide sequences of SEQ ID NO: 1 and SEQ ID NO: 3. Also within the context of the present invention nucleotide sequences are provided which encode one or more of the CDR regions of monoclonal antibody BOIIB2 as identified in SEQ ID NOS: 5 to 10. Particular embodiments of the invention include the sequence encoding scFvs of BOIIB2, as well as sequences having at least 80% sequence identity therewith, most particularly within the regions encoding the CDRs. The present invention also includes complementary sequences which correspond to the monoclonal antibodies, or fragments thereof, mentioned herein. In particular, the present invention includes probes constructed from the monoclonal antibodies, or fragments thereof, mentioned herein or from the polynucleotides or from the complementary sequences mentioned herein.

The nucleotides of the present invention cited above as well as the nucleotide sequence encoding BOIIB2 obtainable from cell line BOIIB2 are useful in the production of antibodies and other antigen-binding fragments, e.g. by recombinant methods. Methods for producing recombinant antibodies and antibody fragments, including cloning and manipulation of antibody genes, production of scFv and other antigen-binding fragments are available in the art. A further aspect thus relates to methods for producing FVIII binding and preferably FVIII-inhibitory molecules by recombinant technology which involve one or more of the nucleotide sequences of the present invention.

Yet another aspect of the present invention further provides a pharmaceutical composition for the prevention or treatment of diseases in which coagulation contributes to the pathology of the disease. Examples of such coagulation disorders include deep vein thrombosis, pulmonary embolism, stroke, myocardial infarction, disorders referred to as SIRS (systemic inflammatory response syndrome).

According to a specific embodiment the antibodies described herein, as well as antigen binding fragments and derivatives thereof are particularly suited for the treatment and/or prevention of coagulation disorders. A further particular embodiment of the invention relates to the use of the antibodies and antibody fragments of the present invention for the prevention and/or treatment of SIRS, more particularly SIRS following acute pancreatitis, ischemia, multiple trauma and tissue injury, haemorrhagic shock, immune-mediated organ injury and infection.

An important aspect of the present invention is that the antibodies, fragments and derivatives thereof allow the treatment and/or prevention of the above-mentioned diseases without the side-effects attributed to or expected with other treatments for coagulation disorders.

A particular embodiment of the present invention relates to pharmaceutical compositions, comprising, as an active ingredient, the monoclonal antibody BOIIB2 or an antigen binding fragment or derivative thereof, in admixture with a pharmaceutically acceptable carrier. The pharmaceutical composition of the present invention should comprise a therapeutically effective amount of the said monoclonal antibody, fragment or derivative, such as indicated hereinafter in respect to the method of treatment or prevention.

According to yet another aspect of the invention pharmaceutical compositions are provided which comprise a combination of two different antibodies to the A2 domain of FVIII according to the present invention or antigen binding fragments or derivatives thereof. More particularly, the two different antibodies both compete with each other for the binding of FVIII. In specific embodiments, the two antibodies bind the same epitope, more particularly the epitope of antibody BOIIB2, but with differing inhibitory activity (e.g. as a result of affinity). Mixing two antibodies capable of competing for the same antigen but with different inhibitory activity in different ratios will allow the production of antibody mixtures with inhibitory activity ranging between the inhibitory activity of each of the antibodies or antigen binding fragments. According to a specific embodiment, one of the two antibodies is antibody BOIIB2 or an antigen-binding fragment thereof.

According to yet another aspect of the invention pharmaceutical compositions are provided which comprise the antibodies or antibody fragments or derivatives of the present invention and another anti-coagulation agent. Suitable other anti-coagulation products, as well as their usual dosage depending on the class to which they belong, are well known to those skilled in the art.

The pharmaceutical compositions of the present invention may further comprise, a therapeutically effective amount of other compounds/drugs active against the disease to be treated.

Suitable pharmaceutical carriers for use in the pharmaceutical compositions of the invention are described for instance in Remington's Pharmaceutical Sciences $16^{th}$ ed. (1980) and their formulation is well known to those skilled in the art. They include any and all solvents, dispersion media, coatings, antibacterial and antifungal agents (for example phenol, sorbic acid, chlorobutanol), isotonic agents (such as sugars or sodium chloride) and the like. Additional ingredients may be included in order to control the duration of action of the monoclonal antibody active ingredient in the composition. Control release compositions may thus be achieved by selecting appropriate polymer carriers such as for example polyesters, polyamino acids, polyvinyl pyrrolidone, ethylene-vinyl acetate copolymers, methylcellulose, carboxymethylcellulose, protamine sulfate and the like. The rate of drug release and duration of action may also be controlled by incorporating the monoclonal antibody active ingredient into particles, e.g. microcapsules, of a polymeric substance such as hydrogels, polylactic acid, hydroxymethylcellulose, polymethyl methacrylate and the other above-described polymers. Such methods include colloid drug delivery systems like liposomes, microspheres, microemulsions, nanoparticles, nanocapsules and so on. Depending on the route of administration, the pharmaceutical composition comprising the active ingredient may require protective coatings. The pharmaceutical form suitable for injectionable use include sterile aqueous solutions or dispersions and sterile powders for the extemporaneous preparation thereof. Typical carriers therefore include biocompatible aqueous buffers, ethanol, glycerol, propylene glycol, polyethylene glycol and mixtures thereof.

The present invention also provides the use of a ligand, namely the monoclonal antibody of the invention as a medicament. More preferably the medicament used in the present invention is a means for preventing and/or treating coagulation disorders. The said ligand may be provided to a patient by any means well known in the art, i.e. orally, intranasally, subcutaneously, intramuscularly, intradermally, intravenously, intraarterially, parenterally or by catheterization.

The present invention therefore provides a method of treatment and/or prevention of coagulation disorders, comprising administering to a mammal in need of such treatment or prevention a therapeutically effective amount of a ligand such as disclosed hereinabove. Preferably the said ligand is human monoclonal antibody of the IgG isotype obtainable from cell line BOIIB2 or an antigen-binding fragment Fab, Fab' or F(ab')$_2$, a complementarity determining region (CDR), a soluble or membrane-anchored single-chain variable fragment or part (scFv), a single variable domain or a derivative or combination of any of these elements.

Yet another aspect of the present invention relates to the use of the monoclonal antibodies and antigen-binding fragments of the invention for the immunological detection of FVIII in human samples and as components of kits suitable for such detection. Methods of immunological detection of an antigen are known in the art and include, but are not limited to ELISA and RIA and immunohistochemical methods. The binding of the antibodies of the present invention to the FVIII antigen can be detected indirectly e.g. by way of a labeled anti-human antibody. Alternatively the antibodies or fragments thereof can be labeled directly.

Yet another aspect of the present invention relates to the use of the anti-FVIII antibody of the present invention and the antigen-binding fragments thereof as a diagnostic tool. The antibodies or antibody fragments of the present invention can be used in the diagnosis of pathological conditions or establishing what the levels of Factor VIII are under normal conditions, e.g. by imaging techniques in which the antibodies or antigen-binding fragments of the invention are labeled and visualized in vivo. A variety of labels for imaging the binding of the antibodies of the present invention in vivo are known in the art and include, but are not limited to optical (e.g. fluorescent), metal, and magnetic labels, each requiring specific (radiation and) detection devices. A particular embodiment of this aspect of the invention relates to the use of the antibodies of the invention in predicting prognosis of the disease and deciding treatment regimen.

Yet another aspect of the present invention relates to the use of the antibodies of the present invention for the screening of compounds which inhibit FVIII, or to identify compounds with advantageuous properties. Combined administration of the compound to be tested and the antibody or fragment of the present invention make it possible to identify whether the compound has an additive effect to the effect observed upon administration of the antibodies or fragments of the invention alone. Other aspects such as counter-effectiveness or toxicity of a compound in combination with an anti-FVIII antibody can also be determined in this way.

The epitope whereto BOIIB2 is binding or the corresponding nucleic acid sequences can be used for different purposes such as for immunization of mammals in order to produce monoclonal IgG antibodies or can be used in an assay for the detection of inhibitory FVIII molecules specifically binding to the epitope of BOIIB2 on the A2-domain of FVIII.

The present invention is further described by the following examples which are provided for illustrative purposes only.

EXAMPLES

The following examples provide a description of the production, characterization and use of a human anti-A2 monoclonal antibody Example 1

Production of a Human Anti-A2 Monoclonal Antibody

Peripheral vein blood was collected after informed consent from a hemophilia A patient with inhibitor. Peripheral blood mononuclear cells (PBMC) were prepared by Ficoll-Hypaque density centrifugation using standard methods. All cell cultures were carried out in Dulbecco's MEM/Nutrient Mix F12 (Life Technologies) supplemented with 10% IgG-free horse serum, 1.5 g/l glucose, 4 mM L-glutamine, 1% Caryoser and 80 mg/l Geomycin.

PBMC were immortalised as follows. $10^7$ PBMC were resuspended in 2 ml culture medium and incubated for 2 h at 37° C. with 200 μl Epstein-Barr virus (EBV) supernatant (B95-8 strain) (14). Cells were then seeded at 300 to 24,000 cells/well in 96-well microtiter plates (Nunc, Roskilde, Denmark) containing 3T6-TRAP cells treated with mitomycin C (50 μg/ml) for 1 h at 37° C., and seeded in culture wells the day prior to EBV infection of PBMC. The 3T6 cell line had been stably transfected with an expression vector for human CD40 ligand (3T6-TRAP). One hundred and fifty μl of culture supernatant were replaced every week by fresh culture medium. After 4 to 8 weeks, depending on growth rate in individual wells, culture supernatants were tested in ELISA for the presence of anti-fVIII antibodies. Positive cell lines were transferred to 24-well plates, and immediately cloned at 60 cells per 96-well plate without feeder cells.

Thus, antibodies towards FVIII are identified by reacting the supernatant with polystyrene plates coated with FVIII or with FVIII in complex with von Willebrand factor (vWF). The binding of specific antibodies is detected by addition of an anti-human IgG reagent coupled to an enzyme. Addition of an enzyme substrate that is converted to a coloured compound in the presence of the enzyme allows the detection of specific antibodies. Such methods referred to as Enzyme-Linked Immuno-Sorbent Assays (ELISA) are well known by those skilled in the art. Detailed description can be found in Current Protocols in Immunology, Chapter 2, John Wiley & Sons, Inc, 1994 (15). B cells producing anti-FVIII antibodies are then expanded and cloned by limiting dilution. Methods to carry out cloning are described for instance in Current Protocols in Immunology, Chapter 2, John Wiley & Sons, Inc, 1994 (15).

Anti-FVIII antibodies having the desired characteristics, namely the capacity to inhibit the pro-coagulant activity of FVIII are identified using commercially available chromogenic assay kits, following the manufacturer's recommendation. Antibodies that inhibit FVIII function with sufficient affinity are selected. FIG. 1 shows the production of an antibody, called BOIIB2, specific for the A2 domain of FVIII.

Antibodies with sufficient binding avidity for FVIII and which inhibit fVIII function are then produced in bulk culture and purified by affinity chromatography using methods well known by those skilled in the art.

Alternatively, antibodies having the required characteristics can be produced by on-purpose immunization in animals. Thus, mice are injected with human FVIII in an adjuvant. Monoclonal anti-human FVIII antibodies are then obtained by fusion of spleen lymphocytes with a mouse myeloma cell line. Cell culture supernatants producing anti-FVIII antibodies are identified and cloned by limiting dilution. A general description of such methods can be found in Current Protocols in Immunology, Chapter 2, John Wiley & Sons, Inc, 1994 (Current Protocols in Immunology (1994) Chapter 2, eds Coligan J E, Kruisbeek A M, Margulies D H, Shevach E M, Strober W, Coico R, National Institute of Health, John Wiley & Sons, Inc). Further selection of inhibitors having the desired characteristics is carried out as described above.

Antibodies produced in mice are then humanized. Thus, sequences of the variable parts of mouse heavy and light chains are aligned with human immunoglobulin variable regions to identify human antibody with the greatest homology in framework regions. The DNA fragment encoding humanized variable regions are then synthesized by PCR-based CDR grafting method as described for instance in Sato et al. (Sato K, et al., 1993, Cancer Research 53: 851-85616). The final PCR product coding for the heavy chain variable part of the humanized antibody is digested and subcloned upstream of the human Cgamma-1 gene in a first expression plasmid. The humanized light chain variable region of the final construction is inserted upstream of the human Ckappa gene in a second expression plasmid. The two constructions are co-transfected into COS cells expression system. A general description of these methods can be found in Sato et al. (above).

Example 2

Characterization Of Anti-A2 Antibody Specificity And Affinity

The specificity of antibodies towards the A2 domain is further characterized in terms of specificity by using a combined transcription-translation system with rabbit reticulocytes, as described (Benhida et al, manuscript in preparation). Briefly, a library of plasmids containing various fragments of the A2 domain is constructed.

The plasmid construct pSP64-FVIII (ATCC, Rockville, Md.) containing the 7.2 Kb full length FVIII cDNA was used as a template to generate all the fragments by PCR. The cDNA fragments carrying mutations or deletions were produced by Splicing by Overlap Extension-PCR (SOE-PCR) (Horton R M and Pease L R., 1991, In: McPherson M J, ed. Directed Mutagenesis: A Practical Approach. Oxford: IRL Press; 217-228; Jacquemin M, et al. 2000, Blood. August 1; 96(3):958-65). For fragments of FVIII of less than 15 amino acids a tag sequence was added including ubiquitin and/or T7 for recognition by specific anti-tag antibodies, together with a complementary sequence of cysteines for S labeling. Polypeptide encoding FVIII fragments were produced in TNT coupled Reticulocyte Lysate Systems (Promega) according to manufacturer's instructions.

Immunoprecipitation of transcribed genes was carried out as follows. Dilutions of samples containing specific antibodies were mixed to 40 μl of protein A Sepharose (Pharmacia) in 500 μl of an appropriate buffer and the mixture gently rocked for 1 hour at 4° C. Unbound antibodies are eliminated by a series of centrifugation and washings. The complex of antibody-protein A Sepharose is resuspended in 300 μl of buffer supplemented by 3 μl of in-vitro L-($^{35}$S) methionine-labeled FVIII polypeptides for an incubation at 4° C. for 2 hours. Bound antigen/antibody complexes are eluted from the beads by boiling for 3 minutes in 30 μl of denaturing sample buffer and the radioactivity counted. A second aliquot is analyzed by SDS-PAGE and visualized by autoradiography.

More detailed, for determination of the epitope of BOIIB2, polypeptides encoding amino acid residues 379-546 corresponding to the wild type sequence of part of the A2 domain of FVIII are produced in TnT coupled Reticulocyte Lysate Systems (Promega, Buckingham, London, UK) according to the manufacturer's instructions. This system includes a combined transcription-translation provided by rabbit reticulocytes. Additionally, polypeptides encoding 379-546 including mutations R484A; Y487A; R489A and P492A, and a polypeptide encoding 461-531 were also produced. Polypeptides are radiolabeled by addition of $^{35}$S-methionine in the reaction mixture. BOIIB2 antibody is incubated with a Protein-A Sepharose, washed and resuspended before addition of one of the radiolabeled polypeptides. The suspension is incubated for 90 minutes at room temperature, washed and the labeled polypeptide eluted from Sepharose beads by addition of a sodium-dodecylsulfate containing buffer. The presence of labeled polypeptide (evaluated by scintillation counting) indicates that BOIIB2 has a binding site on such peptide.

FIG. 2 shows the results of such an experiment for antibody BOIIB2. A binding site in the region encompassing residues 389 to 510 is identified in the A2 domain. However, further delineation of the epitope was difficult as trimming off either the amino-terminal or the carboxy-terminal end of such fragment rapidly abolished antibody binding. We therefore proceeded by a stepwise approach in which single mutations were introduced in the presumed main binding site, namely 484-509. FIG. 2 shows that single mutations in such a site abolished antibody binding. Further, single mutations were introduced into the sequence of 3 glutamic acids located in 389-391 (Lubin I M et al. 1997, J Biol Chem. 28; 272(48): 30191-519), which also resulted in a loss of binding (data not shown). It could therefore be concluded that the binding site was located within the 484-509 amino acid sequence, but that 3 glutamic acids were required at a distance for efficient antibody binding.

Antibody affinity is calculated using the surface plasmon resonance system (O'Shanessy D J, et al. 1993, Anal Biochem 212:457-462). Thus, real-time kinetic interaction between FVIII and hu-mAbs was analyzed using a Pharmacia Biosensor BIAcore™ instrument (Pharmacia Biosensor AB). Purified BOIIB2 (20 μg/ml in 10 mM sodium acetate buffer pH 5.0) was immobilized on the activated surface of a CM5 sensor chip, according to the manufacturer's instructions. All binding experiments were carried out in HBS at a constant flow rate of 10 μ/min. FVIII in HBS was infused at various concentrations over the ECR-immobilized sensor chip surface. At the end of each cycle, the surface was regenerated by flushing HCl, pH 2, for 36 sec. Association and dissociation rate constants were determined using the BIA evaluation software package, according to models assuming the binding of one analyte to one or two immobilized ligand(s).

BOIIB2 was $k_{diss}$ was evaluated as $1\times10^{-8}$ $s^{-1}$ and the $k_{ass}$ as $1\times10^{3}$ $M^{-1}s^{-1}$.

Example 3

Sequencing of BOIIB2 Antibody

The isolation of RNA from EBV-immortalized human B cell lines was carried out using TRIzol Reagent according to the manufacturer's instructions (Life Technologies). cDNA was synthesized with the SuperScript pre-amplification system for first-strand cDNA synthesis. The cDNA encoding the heavy chain variable region genes (VH) was amplified by PCR using primers specific for the leader sequence of the VH families and for the first exon of the Cgamma region, as described (Jacquemin M, et al. 2000, Blood 1; 95(1):156-63). Annealing was performed at 60° C. for 40 PCR cycles. PCR products of the appropriate size (460 bp) were isolated from 1.5% agarose gel and cloned using the TA Cloning Kit (Invitrogen BV, Leek, The Netherlands). A PCR screening using couples of primers corresponding to the $V_H$ gene family of interest was carried out on cultures of randomly-selected colonies. Plasmid DNA from positive colonies was isolated using Wizard Plus Minipreps (Promega, Menlo Park, Calif.) and sequenced in both directions with Sequenase (United States Biochemical, Cleveland, Ohio), according to manufacturer's instructions. Analysis of the variable gene sequences was made using the "V BASE Sequence Directory" (Tomlinson et al., MRC Centre for protein Engineering, Cambridge, UK).

BOIIB2 $V_H$ gene belongs to the VH4 group and is most homologous to DP-71. The J segment was most homologous to JH6c. Sequencing of the cloned light chain gene identified the $V_L$ as a $V_{kappa}$III and the J segment as a $J_{kappa}$5. (FIG. 3)

FIG. 3 shows the whole sequence of the antibody with leader peptide sequence. The invention also relates to the antibody without the leader sequence. Sequences obtained were as following:

Example 4

Production Of Monoclonal Antibody Fragments Or Derivatives

Fragments of monoclonal antibodies or derivatives can be used for the purpose of the present invention. Proteolytic digestion of antibody using well described methods (Stanworth D and Turner M W, 1978, in Chapter 6, Immunochemistry, vol 1 of Handbook of Experimental Immunology, ed Weir D M, Blackwell Scientific Publications) generates either $F(ab')_2$ or Fab fragments. Such fragments, which contain the antibody-binding site, have lost a number of properties of the parent antibody, such as complement activation or capacity to bind to Fc gamma receptors.

Soluble or membrane anchored single-chain variable parts of the antibodies can be obtained. The DNA sequences of the variable parts of human heavy and light chains are amplified in separated reactions and inserted into a TA cloning vector. A 15-aminoacid linker sequence, such as (Gly4 Ser)3, is inserted between VH and VL by a two-step PCR. The resulting fragment is inserted in a suitable vector for expression of scFv as soluble or phage-displayed polypeptide. Description of such methods can be found in Gilliland et al. (1996, Tissue Antigens 47: 1-20).

Peptides representative of all or part of the hypervariable region of an antibody can be obtained by synthesis using an applied biosystem synthesizer or related technology. Such peptides alone or in combination exert properties similar to that of the parent antibody.

Alternatively, peptides comprising one or more, more particularly two or more CDR regions of an antibody can be produced by recombinant methods.

Antibodies which are homologuous to BOIIB2 for example with 80% homology and with the same or higher affinity to FVIII can be obtained by known methods in the art. Mutations of the amino acids sequences, more in particular in the variable region or yet more in particular in the CDRs can be made by standard methods. This can be followed by testing the affinity of the obtained mutants in affinity assays, testing the inhibtory capacity and testing whether the epitope has remained the same with methods as described herein. In this way antibodies can be obtained with modified amino acid sequences which are homologuous to BOIIB2. Alternatively, mutations in the framework regions between the CDRs can be made by standard methods. This can be followed by checking whether the affinity and the inhibitory capacity of the obtained mutants is affected.

Example 5

Use of Antibodies Of The Present Invention

Establishing the 3-D Conformation of FVIII Heavy Chain

The C2 domain is the only domain of FVIII that has been crystallized so far. However, the validation of the model structure required the co-crystallization of the C2 domain with a specific antibody. Thus, the putative phospholipid binding sites located on the C2 domain structure were confirmed by binding of an antibody recognizing these sites and inhibiting the binding of the whole FVIII molecule to phospholipids. Single aminoacid substitutions in such sites further confirmed their functional role.

Experimental conditions to form crystals with antibodies are well established (see for instance Spiegel P C et al. 2001, Blood. July 1; 98(1):13-9). The co-precipitation of A2 with an antibody of sufficient affinity greatly facilitates the determination of appropriate starting conditions.

Mechanism of FVIII Inactivation

One of the main mechanisms by which FVIII is inactivated is through the dissociation of the A2 domain, which is bound non-covalently to the heterodimer made of A1 and A3-C1-C2 (26). Antibodies recognizing the A2 domain can inhibit FVIII function by accelerating the dissociation of A2. The biochemical events leading to the physiological dissociation of A2 are well established (Jenkins P V et al. 2004, Biochemistry. May 4; 43(17):5094-101).

Another mechanism by which an antibody to the 480-509 region of the A2 domain of FVIII can inhibit the functional activity is by interfering with the binding of FIXa. The latter has a low affinity binding site precisely mapped to the same region on FVIII. The binding of an antibody such as BOIIB2 can therefore prevent the conformational changes required for full FIXa enzymatic activity.

FIG. 1 shows the results of the evaluation of the capactity of the BOIIB2 to inhibit FVIII in a functional assay.

As functional assay, we used a chromogenic assay in which trombin-activated FVIII acts as a cofactor to factor IXa in the conversion of factor X to factor Xa. Briefly, 20 µl of recFVIII diluted in PBS-BSA solution (1 IU/ml) were mixed with equal volume of serial dilution of BOIIB2 in same PBS-BSA solution (X axe) and incubated for 1 hoo at 37° C. Twenty µl of the mixture were then incubated for 3 min. at R.T. in microtiter well with 20 µl of the reactif 1 (factor X) and 20 µl of the reactif 2 (factor Ixa) before addition of 100 µl of the reactif 3 (chromogenic substrate and stop buffer). Control experiments included recFVIII incubated without specific antibodies or with the same concentration of non relevant antibodies. The density of the substrate coloration is directly measured at 405 nm with a reference at 450 nm. Percentage of inhibition (Y axe) is calculated with regard to the positive control recFVIII1 IU/ml. The curve indicated that BOIIB2 inhibits FVIII function up to 99% at concentration of 0.1 µg/ml.

FVIII Clearance Mechanisms

One mechanism by which FVIII is cleared off from the circulation is by binding to the low density lipoprotein receptor family (LPR). At least two binding sites for the LPR receptor have been mapped in the FVIII molecule, in the A2 and C2 domains. The site mapped to the A2 domain has been further characterized by single aminoacid substitution and found to correspond to the sequence 484-510, which overlaps with the antibody-binding site identified for antibody BOIIB2 in the present invention. BOIIB2 can therefore be used to establish the importance of this clearance mechanism in the total clearance of FVIII.

Thus, haemophilia A mice are injected IV with either 2IU of recombinant FVIII or with a mixture made by preincubating 2IU recombinant FVIII with BOIIB2. The clearance rate of FVIII from the circulation is established by bleeding mice at regular time intervals and determining residual FVIII activity by an antigen-specific ELISA.

Example 6

Evaluation of the Thrombin Generation in a Platelet Rich Plasma (PRP) in Presence of the BOIIB2 Antibody Blood is collected in tubes with citrate buffer (9 volumes of blood to 1 volume of 129 mM sodium citrate). The tubes are centrifuged for 15 minutes at 900 rpm. The PRP is pipetted off after centrifugation and collected. Platelet count is measured in a Coulter Counter. A platelet poor plasma is used to adjust the PRP to 300000 platelets/µl. 80 µl of PRP are incubated during 5 minutes with 20 µl of Hepes Buffer (hepes 20 mM, NaCl 140 mM, BSA 5 mg/ml, pH 7.35) containing the BOIIB2 antibody (3 µg/ml) plus SynthAsil beads (Instrumentation Laboratory) 1/200 or Innovin (Dade Behring) 1/7500. The SynthAsil beads negatively charged, allow activation of the intrinsic pathway of coagulation, whereas Innovin, containing only Tissue Factor, allows activation of the extrinsic pathway. 20 µl of substrate (Z-Gly-Gly-Arg-AMC) (Bachem; Bubbendorf, Switzerland) solubilized in pure DMSO and diluted in a developing solution (Hepes 20 mM, BSA 60 mg/ml, pH 7.35, CaCl2 1 m), are added to the different samples. Upon splitting by thrombin, it releases the fluorescent AMC (7-amino-4-methylcoumarin) After 3 minutes, absorbance is read at 390 nm excitation/460 mm emission filter set, on a Thrombinoscope™.

FIGS. 5 and 6 show that BOIIB2 fully inhibits thrombin production by the intrinsic pathway as well as by the extrinsic pathway of coagulation.

Example 7

Identification of Antibodies as Antibodies Competing With Antibody BOIIB2

Antibodies directed against FVIII are either generated by traditional monoclonal antibody techniques or obtained from hemophilia A patients with inhibitor.

To identify whether the factor VIII binding antobodies compete with antibody BIIIB2, the following method is used. A polystyrene microtitration plate is incubated overnight at 4° C. with 50 µL antibody at 2 microgram/ml in phosphate buffered saline (PBS). The plates are then washed 4 times with PBS-Tween. Biotinylated recombinant FVIII (0.5 microgram/ml) in Tris-BSA-Tween is mixed with the antibody or with BOIIB2 at various concentrations before addition to the antibody coated plates. After a two hour incubation period at 4° C., the plates are washed 4 times and bound biotinylated FVIII is detected by addition of avidine peroxidase (Sigma) at 1 microgram/ml. After 30 min at RT, the plates are washed again and supplemented with 100 µL OPD. The resulting OD is read at 490 nm in a Emax Microplate Reader (Molecular Devices, Menlo Park, Calif.).

Biotinylated FVIII for use in the above experiment is prepared by incubating recombinant FVIII (100 microgram/ml) dialysed in Hepes buffer (Hepes10 mM, NaCl 0.15 M, CaCl2 10 mM, pH 8.5) with sulfo-NHS-LC-biotin (Pierce) at 1 microgram/ml for 2 hours at RT. The preparation is then dialysed against Hepes buffer and stored and −80° C.

The invention claimed is:

1. An isolated human monoclonal antibody of the IgG isotype, or an antigen-binding fragment thereof, which specifically binds to the A2 domain of Factor VIII (FVIII) and wherein, the heavy chain of the variable region of said antibody comprises, in its CDRs, the sequences of SEQ ID NOS: 5, 6, and 7, and the light chain variable region of said antibody comprises, in its CDRs, the sequences of SEQ ID NOS: 8, 9, and 10.

2. The isolated human monoclonal antibody according to claim 1, characterized in that the heavy chain of the variable region of the antibody comprises the sequence of SEQ ID NO: 2, and the light chain variable region comprises the sequence of SEQ ID NO: 4.

3. The isolated human monoclonal antibody according to claim 2, which is BOIIB2, produced by the cell line deposited with accession number LMBP 6422CB at the BCCM.

4. The antigen-binding fragment according to claim 1, which is selected from the group consisting of a Fab, Fab' or F(ab')$_2$, a diabody, a triabody, a tetrabody, a minibody, and a soluble or membrane-anchored single-chain variable part.

5. A cell line producing the antibody according to claim 1.

6. A polynucleotide encoding for an antibody or an antigen-binding fragment which specifically binds to the A2 domain of FVIII, said antibody or antigen-binding fragment comprising the sequences of SEQ ID NOS: 5, 6, and 7 and the sequences of SEQ ID NOS: 8, 9, and 10.

7. A recombinant expression vector comprising the nucleotide sequence of claim 6.

8. A method of detecting FVIII in a human sample, said method comprising the step of contacting the sample with an antibody or antigen-binding fragment, which specifically binds to the A2 domain of FVIII and wherein the heavy chain of the variable region of said antibody comprises, in its CDRs, the sequences of SEQ ID NOS: 5, 6, and 7, and the light chain variable region of said antibody comprises, in its CDRs, the sequences of SEQ ID NOS: 8, 9, and 10.

9. A method of treatment of a thrombotic pathological condition in a mammal, wherein the method comprises administering to a mammal in need of such treatment, a therapeutically effective amount of a human monoclonal antibody of the IgG isotype, or an antigen-binding fragment thereof, which specifically binds to the A2 domain of FVIII, wherein the heavy chain of the variable region of said antibody comprises, in its CDRs, the sequences of SEQ ID NOS: 5, 6, and 7, and the light chain variable region of said antibody comprises, in its CDRs, the sequences of SEQ ID NOS: 8, 9, and 10.

10. The method according to claim 9, wherein said thrombotic pathological condition is selected from the group consisting of deep vein thrombosis, pulmonary embolism, stroke, myocardial infarction, and SIRS (systemic inflammatory response syndrome).

11. The method according to claim 10, wherein said thrombotic pathological condition is selected from the group consisting of sepsis, septic shock, thrombus formation in the microvasculature, disseminated intravascular coagulation (DIC), and septicemia.

* * * * *

UNITED STATES PATENT AND TRADEMARK OFFICE
CERTIFICATE OF CORRECTION

| | | |
|---|---|---|
| PATENT NO. | : 7,858,089 B2 | Page 1 of 1 |
| APPLICATION NO. | : 11/997283 | |
| DATED | : December 28, 2010 | |
| INVENTOR(S) | : Jacquemin et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 56 days.

Signed and Sealed this

Nineteenth Day of July, 2011

David J. Kappos
*Director of the United States Patent and Trademark Office*